(12) United States Patent
Huang et al.

(10) Patent No.: US 11,767,504 B2
(45) Date of Patent: Sep. 26, 2023

(54) ALBUMIN COMPOSITIONS AND METHODS OF PRODUCING AND USING SAME

(71) Applicant: Albcura Corporation, New Taipei (TW)

(72) Inventors: Po-Yi Huang, Taipei (TW); Meng-Tsung Hsu, Changhua (TW); Pei-Chin Chen, New Taipei (TW); Yu-Feng Liang, Tainan (TW); Chen-Yu Hsieh, New Taipei (TW); Jeffy Chern, Kaohsiung (TW)

(73) Assignee: Albcura Corporation, New Taipei (TW)

(*) Notice: Subject to any disclaimer, the term of this patent is extended or adjusted under 35 U.S.C. 154(b) by 315 days.

(21) Appl. No.: 16/994,342

(22) Filed: Aug. 14, 2020

(65) Prior Publication Data

US 2022/0048976 A1   Feb. 17, 2022

(51) Int. Cl.
*C07K 1/00* (2006.01)
*C12N 5/00* (2006.01)
C07K 14/765 (2006.01)
C12N 5/074 (2010.01)
C12N 5/0735 (2010.01)

(52) U.S. Cl.
CPC .......... *C12N 5/0018* (2013.01); *C07K 14/765* (2013.01); *C12N 5/0606* (2013.01); *C12N 5/0696* (2013.01); *C12N 2500/30* (2013.01)

(58) Field of Classification Search
CPC .. C07K 14/765; C12N 5/0018; C12N 5/0606; C12N 5/0696; C12N 2500/30
See application file for complete search history.

(56) References Cited

U.S. PATENT DOCUMENTS

| | | | |
|---|---|---|---|
| 5,440,018 A | 8/1995 | Ohmura et al. | |
| 6,277,828 B1 | 8/2001 | Knepp et al. | |
| 8,609,416 B2 | 12/2013 | Barnett | |
| 2014/0234966 A1 | 8/2014 | Merkel et al. | |
| 2016/0075993 A1 | 3/2016 | Kuriyama et al. | |

FOREIGN PATENT DOCUMENTS

| | | | | |
|---|---|---|---|---|
| JP | 6634822 B2 | 1/2020 | | |
| WO | WO 2019/055853 A1 | * | 3/2019 | ........... C12N 5/0783 |

OTHER PUBLICATIONS

Simard et al.: Locating high-affinity fatty acid-binding sites on albumin by x-ray crystallography and NMR spectroscopy. Proceedings of the National Academy of Sciences: Dec. 13, 2005 vol. 102 No. 50 (Year: 2005).*
Cellastim—Safety Data Sheet (Year: 2018).*
Wang et al (Protein aggregation—Pathways and influencing factors: International Journal of Pharmaceutics 390, pp. 89-97 (Year: 2010).*
Else (The highly unnatural fatty acid profile of cells in culture: Progress in Lipid Research—vol. 77. Article 101017 pp. 1-19 (Year: 2019).*
Albcura. deAlbumin® Chemical-Defined Recombinant Albumin for a robust cell culture. BioJapan Yokohama 2018. Pacifico Yokohama, Japan. Oct. 10-12, 2018. 2 pages. (Flyer).
Albcura. deAlbumin® Chemically-Defined Recombinant Albumin for a robust cell culture. The 17th Congress of the Japanese Society for Regenerative Medicine (17JSRM). Pacifico Yokohama, Japan. Mar. 21-23, 2018. 2 pages. (Flyer).
Altschul, et al. Basic local alignment search tool. J Mol Biol. Oct. 5, 1990;215(3):403-410. doi: 10.1016/S0022-2836(05)80360-2.
Altschul, et al. Gapped BLAST and PSI-BLAST: a new generation of protein database search programs. Nucleic Acids Res. Sep. 1, 1997; 25(17):3389-3402. doi: 10.1093/nar/25.17.3389.
Chen, et al. Chemically defined conditions for human iPS cell derivation and culture. Nat Methods. May 2011; 8(5): 424-429. doi:10.1038/nmeth.1593.
Chen R.F. Removal of Fatty Acids From Serum Albumin by Charcoal Treatment. J Biol Chem. Jan. 25, 1967;242(2):173-181.
Finn, et al. Serum Albumin Prevents Protein Aggregation and Amyloid Formation and Retains Chaperone-like Activity in the Presence of Physiological Ligands. J Biol Chem. Jun. 15, 2012;287(25):21530-21540. doi: 10.1074/jbc.M112.372961. Epub May 1, 2012.
Invitria. Optibumin—Recombinant Human Albumin (rHSA). 2 pages. Retrieved online Dec. 15, 2019 at URL: invitria.com/cell-culture-products/optibumin-lipid-reduced-recombinant-human-albumin-rhsa/.
Karlin, et al. Applications and statistics for multiple high-scoring segments in molecular sequences. Proc Natl Acad Sci USA. Jun. 15, 1993; 90(12):5873-5877. doi: 10.1073/pnas.90.12.5873.
Karlin, et al. Methods for assessing the statistical significance of molecular sequence features by using general scoring schemes. Proc Natl Acad Sci USA. Mar. 1990; 87(6): 2264-2268. doi: 10.1073/pnas.87.6.2264.

(Continued)

*Primary Examiner* — Yong D Pak
(74) *Attorney, Agent, or Firm* — Anne M. Reynolds; Casimir Jones, S.C.

(57) ABSTRACT

Disclosed herein are albumin compositions having defined fatty acid profiles and methods of using the same. The albumin compositions described herein are suitable for use in cell culture methods, protein stabilization methods, amongst others. The albumin compositions described herein may improve the viability of and/or promote the growth of cells (e.g., mammalian cells) when the cells are cultured in a medium containing the albumin compositions. The albumin compositions described herein may improve the stability of a biologic when the biologic is in the presence of the albumin compositions. Further provided herein are methods of formulating albumin compositions having defined fatty acid profiles as described herein.

24 Claims, 9 Drawing Sheets

Specification includes a Sequence Listing.

(56) References Cited

OTHER PUBLICATIONS

Sargent B. Albumin Fatty Acid Profiles for cell culture media—Enabling Albumin Optimization for Cell Culture Media. Cell Culture Dish. Part 3 of the Cell Culture Media Optimization Series. Jun. 15, 2016. 9 pages. Retrieved online Dec. 15, 2019 at URL: cellculturedish.com/albumin-fatty-acid-profiles-for-cell-culture-media-enabling-albumin-optimization-for-cell-culture-media/.

Wootton, et al. Statistics of local complexity in amino acid sequences and sequence databases. Computers & Chemistry. Jun. 1993; 17(2): 149-163. doi: 10.1016/0097-8485(93)85006-X.

Wu, et al. Oleate but not stearate induces the regulatory phenotype of myeloid suppressor cells. Sci Rep 7:7498. Aug. 8, 2017. pp. 1-14. DOI:10.1038/s41598-017-07685-9.

* cited by examiner

ALBUMIN COMPOSITIONS AND METHODS OF PRODUCING AND USING SAME

SEQUENCE LISTING

The instant application contains a Sequence Listing which has been submitted electronically in ASCII format and is hereby incorporated by reference in its entirety. Said ASCII copy, created on Jul. 24, 2020, is named 57899-701_201_SL.txt and is 10,704 bytes in size.

BACKGROUND

Albumin is a family of globular, water-soluble proteins that are commonly found in blood plasma. Albumins are generally transport proteins that are capable of binding to various ligands, such as fatty acids, enzymes, hormones, and trace elements. Albumins are commonly used in the culturing of cells (e.g., stem cells) as well as an excipient (e.g., to stabilize biologics). The performance of various albumin compositions varies considerably and may be due, in part, to the fatty acid make-up of the composition. For example, the presence of some fatty acids have been reported to inhibit cell growth and/or viability. Furthermore, albumin compositions may vary considerably from batch to batch, thereby decreasing the reliability of the product.

SUMMARY

The disclosure herein addresses the considerable unmet need for albumin compositions with defined and consistent fatty acid profiles for the use in cell culture methods and as excipients.

In one aspect, a composition is provided comprising: a) an albumin polypeptide; b) one or more fatty acids having less than 18 carbon atoms present at a molar ratio to the albumin polypeptide ranging from about 0.02 to about 0.4; and c) one or more fatty acids having 18 carbon atoms or more present at a molar ratio to the albumin polypeptide ranging from about 0.03 to about 0.6, wherein the composition is substantially free of pentadecanoic acid (C15:0), margaric acid (C17:0), and/or heptadecenoic acid (C17:1 ω-7). In some cases, the one or more fatty acids having less than 18 carbon atoms comprises one or more fatty acids selected from the group consisting of: lauric acid (C12:0), myristic acid (C14:0), palmitic acid (C16:0), and palmitoleic acid (C16:1). In some cases, the one or more fatty acids having less than 18 carbon atoms consists of lauric acid (C12:0), myristic acid (C14:0), palmitic acid (C16:0), and palmitoleic acid (C16:1). In some cases, the one or more fatty acids having 18 carbon atoms or more comprises one or more fatty acids selected from the group consisting of: stearic acid (C18:0), oleic acid (C18:1ω-9), linoleic acid (C18:2), and eicosadienoic acid (C20:2 ω-6). In some cases, the one or more fatty acids having 18 carbon atoms or more consists of stearic acid (C18:0), oleic acid (C18:1ω-9), linoleic acid (C18:2), and eicosadienoic acid (C20:2 ω-6). In some cases, the one or more fatty acids having 18 carbon atoms or more further comprises one or more fatty acids selected from the group consisting of: bishomo-γ-linolenic acid (C20:3 arachidonic acid (C20:4), docosatetraenoic acid (C22:4 ω-6), and docosahexaenoic acid (C22:6 ω-3). In some cases, (i) the one or more fatty acids having less than 18 carbon atoms consists of lauric acid (C12:0), myristic acid (C14:0), palmitic acid (C16:0), and palmitoleic acid (C16:1); and (ii) the one or more fatty acids having 18 carbon atoms or more consists of stearic acid (C18:0), oleic acid (C18:1ω-9), linoleic acid (C18:2), eicosadienoic acid (C20:2 ω-6), bishomo-γ-linolenic acid (C20:3 arachidonic acid (C20:4), docosatetraenoic acid (C22:4 ω-6), and docosahexaenoic acid (C22:6 ω-3). In some cases, (i) the one or more fatty acids having less than 18 carbon atoms consists of lauric acid (C12:0), myristic acid (C14:0), palmitic acid (C16:0), and palmitoleic acid (C16:1); and (ii) the one or more fatty acids having 18 carbon atoms or more consists of stearic acid (C18:0), oleic acid (C18:1ω-9), linoleic acid (C18:2), and eicosadienoic acid (C20:2 ω-6). In some cases, (i) the one or more fatty acids having less than 18 carbon atoms consists of lauric acid (C12:0), myristic acid (C14:0), palmitic acid (C16:0), and palmitoleic acid (C16:1); and (ii) the one or more fatty acids having 18 carbon atoms or more consists of stearic acid (C18:0), oleic acid (C18:1ω-9), linoleic acid (C18:2), eicosadienoic acid (C20:2 ω-6), bishomo-γ-linolenic acid (C20:3 ω-6), and arachidonic acid (C20:4). In some cases, a total molar ratio of fatty acid to the albumin polypeptide is less than 1. In some cases, the composition is substantially free of α-linolenic acid (C18:3), γ-linolenic acid (C18:3), arachidic acid (C20:0), eicosatrienoic acid (C20:3 eicosapentaenoic acid (C20:5 behenic acid (C22:0), docosapentaenoic acid (C22:5 ω-3), lignoceric acid (C24:0), and/or cerotic acid (C26:0). In some cases, the one or more fatty acids having less than 18 carbon atoms and the one or more fatty acids having 18 carbon atoms or more are both adsorbed to the albumin polypeptide.

In another aspect, a composition is provided comprising: a) an albumin polypeptide; b) lauric acid (C12:0) present at a molar ratio to the albumin polypeptide ranging from about 0.001 to about 0.008; c) myristic acid (C14:0) present at a molar ratio to the albumin polypeptide ranging from about 0.001 to about 0.022; d) palmitic acid (C16:0) present at a molar ratio to the albumin polypeptide ranging from about 0.02 to about 0.3; e) palmitoleic acid (C16:1) present at a molar ratio to the albumin polypeptide ranging from about 0.002 to about 0.03; 0 stearic acid (C18:0) present at a molar ratio to the albumin polypeptide ranging from about 0.011 to about 0.2; g) oleic acid (C18:1ω-9) present at a molar ratio to the albumin polypeptide ranging from about 0.02 to about 0.3; h) linoleic acid (C18:2) present at a molar ratio to the albumin polypeptide ranging from about 0.0002 to about 0.12; and i) eicosadienoic acid (C20:2 ω-6) present at a molar ratio to the albumin polypeptide ranging from about 0.0001 to about 0.002. In some cases, the composition further comprises bishomo-γ-linolenic acid (C20:3 ω-6) present at a molar ratio to the albumin polypeptide ranging from about 0.0003 to about 0.002. In some cases, the composition further comprises arachidonic acid (C20:4) present at a molar ratio to the albumin polypeptide ranging from about 0.001 to about 0.01. In some cases, the composition further comprises docosatetraenoic acid (C22:4 ω-6) present at a molar ratio to the albumin polypeptide ranging from about 0.0009 to about 0.003. In some cases, the composition further comprises docosahexaenoic acid (C22:6 ω-3) present at a molar ratio to the albumin polypeptide ranging from about 0.0003 to about 0.001. In some cases, a total molar ratio of fatty acid to the albumin polypeptide is from about 0.06 to about 1. In some cases, the composition is substantially free of pentadecanoic acid (C15:0), margaric acid (C17:0), heptadecenoic acid (C17:1 ω-7), α-linolenic acid (C18:3), γ-linolenic acid (C18:3), arachidic acid (C20:0), eicosatrienoic acid (C20:3 eicosapentaenoic acid (C20:5 behenic acid (C22:0), docosapentaenoic acid (C22:5 ω-3), lignoceric acid (C24:0), and/or cerotic acid (C26:0).

In another aspect, a composition is provided comprising: a) an albumin polypeptide; and b) one or more fatty acids, wherein the composition is substantially free of one or more of pentadecanoic acid (C15:0), margaric acid (C17:0), heptadecenoic acid (C17:1 ω-7), α-linolenic acid (C18:3), γ-linolenic acid (C18:3), arachidic acid (C20:0), eicosatrienoic acid (C20:3 ω-3), eicosapentaenoic acid (C20:5 behenic acid (C22:0), docosapentaenoic acid (C22:5 ω-3), lignoceric acid (C24:0), and cerotic acid (C26:0), and wherein a total molar ratio of the one or more fatty acids to the albumin polypeptide is from about 0.05 to about 1.

In yet another aspect, a composition is provided comprising: a) an albumin polypeptide; and b) fatty acids, wherein the fatty acids consist of: i) lauric acid (C12:0); ii) myristic acid (C14:0); iii) palmitic acid (C16:0); iv) palmitoleic acid (C16:1); v) stearic acid (C18:0); vi) oleic acid (C18:1ω-9); vii) linoleic acid (C18:2); viii) eicosadienoic acid (C20:2 ω-6); ix) bishomo-γ-linolenic acid (C20:3 ω-6); x) arachidonic acid (C20:4); xi) docosatetraenoic acid (C22:4 ω-6); and xii) docosahexaenoic acid (C22:6 ω-3), wherein a total molar ratio of the fatty acids to the albumin polypeptide is less than about 1. In some cases, the lauric acid (C12:0) is present at a molar ratio to the albumin polypeptide of less than about 0.01; the myristic acid (C14:0) is present at a molar ratio to the albumin polypeptide of less than about 0.05; the palmitic acid (C16:0) is present at a molar ratio to the albumin polypeptide of less than about 0.5; the palmitoleic acid (C16:1) is present at a molar ratio to the albumin polypeptide of less than about 0.05; the stearic acid (C18:0) is present at a molar ratio to the albumin polypeptide of less than about 0.2; the oleic acid (C18:1ω-9) is present at a molar ratio to the albumin polypeptide of less than about 0.5; the linoleic acid (C18:2) is present at a molar ratio to the albumin polypeptide of less than about 0.2; the eicosadienoic acid (C20:2 ω-6) is present at a molar ratio to the albumin polypeptide of less than about 0.005; the bishomo-γ-linolenic acid (C20:3 ω-6) is present at a molar ratio to the albumin polypeptide of less than about 0.005; the arachidonic acid (C20:4) is present at a molar ratio to the albumin polypeptide of less than about 0.01; the docosatetraenoic acid (C22:4 ω-6) is present at a molar ratio to the albumin polypeptide of less than about 0.005; the docosahexaenoic acid (C22:6 ω-3) is present at a molar ratio to the albumin polypeptide of less than about 0.005; or any combination thereof.

In yet another aspect, a composition is provided comprising: a) an albumin polypeptide; and b) fatty acids, wherein the fatty acids consist of: i) lauric acid (C12:0); ii) myristic acid (C14:0); iii) palmitic acid (C16:0); iv) palmitoleic acid (C16:1); v) stearic acid (C18:0); vi) oleic acid (C18:1ω-9); vii) linoleic acid (C18:2); and viii) eicosadienoic acid (C20:2 ω-6). In some cases, the lauric acid (C12:0) is present at a molar ratio to the albumin polypeptide of less than about 0.005; the myristic acid (C14:0) is present at a molar ratio to the albumin polypeptide of less than about 0.005; the palmitic acid (C16:0) is present at a molar ratio to the albumin polypeptide of less than about 0.05; the palmitoleic acid (C16:1) is present at a molar ratio to the albumin polypeptide of less than about 0.005; the stearic acid (C18:0) is present at a molar ratio to the albumin polypeptide of less than about 0.05; the oleic acid (C18:1ω-9) is present at a molar ratio to the albumin polypeptide of less than about 0.05; the linoleic acid (C18:2) is present at a molar ratio to the albumin polypeptide of less than about 0.0005; the eicosadienoic acid (C20:2 ω-6) is present at a molar ratio to the albumin polypeptide of less than about 0.0005; or any combination thereof.

In yet another aspect, a composition is provided comprising: a) an albumin polypeptide; and b) fatty acids, wherein the fatty acids consist of: i) lauric acid (C12:0); ii) myristic acid (C14:0); iii) palmitic acid (C16:0); iv) palmitoleic acid (C16:1); v) stearic acid (C18:0); vi) oleic acid (C18:1ω-9); vii) linoleic acid (C18:2); viii) eicosadienoic acid (C20:2 ω-6); ix) bishomo-γ-linolenic acid (C20:3 ω-6); and x) arachidonic acid (C20:4). In some cases, the lauric acid (C12:0) is present at a molar ratio to the albumin polypeptide of less than about 0.005; the myristic acid (C14:0) is present at a molar ratio to the albumin polypeptide of less than about 0.01; the palmitic acid (C16:0) is present at a molar ratio to the albumin polypeptide of less than about 0.1; the palmitoleic acid (C16:1) is present at a molar ratio to the albumin polypeptide of less than about 0.01; the stearic acid (C18:0) is present at a molar ratio to the albumin polypeptide of less than about 0.1; the oleic acid (C18:1ω-9) is present at a molar ratio to the albumin polypeptide of less than about 0.5; the linoleic acid (C18:2) is present at a molar ratio to the albumin polypeptide of less than about 0.05; the eicosadienoic acid (C20:2 ω-6) is present at a molar ratio to the albumin polypeptide of less than about 0.0005; the bishomo-γ-linolenic acid (C20:3 ω-6) is present at a molar ratio to the albumin polypeptide of less than about 0.0005; the arachidonic acid (C20:4) is present at a molar ratio to the albumin polypeptide of less than about 0.005; or any combination thereof.

In any of the preceding aspects, the albumin polypeptide is derived from human or bovine. In any of the preceding aspects, the albumin polypeptide is a recombinant albumin polypeptide. In any of the preceding aspects, the recombinant albumin polypeptide is purified from bacteria, yeast, or rice. In any of the preceding aspects, the yeast is of the species *Pichia pastoris, Saccharomyces cerevisiae*, or *Kluyveromyces lactis*. In any of the preceding aspects, the rice is of the species *Oryza sativa*. In any of the preceding aspects, the albumin polypeptide is derived from plasma or serum. In any of the preceding aspects, the albumin polypeptide is a defatted albumin polypeptide.

In another aspect, a cell culture medium is provided comprising the composition of any one of the preceding aspects, and a basal medium. In some cases, the composition is present in the cell culture medium at a concentration from about 0.01% (w/w) to about 10% (w/w), or from about 0.1 mg/mL to about 100 mg/mL.

In another aspect, a method is provided comprising incubating biological cells in the cell culture medium of any one of the preceding aspects. In some cases, the biological cells are eukaryotic cells. In some cases, the eukaryotic cells are stem cells. In some cases, the stem cells are induced pluripotent stem (iPS) cells, embryonic stem (ES) cells, or mesenchymal stem cells (MSCs). In some cases, the eukaryotic cells are T-cells. In some cases, the eukaryotic cells are neuronal cells. In some cases, the method results in an increase in viable cell density of the biological cells as compared to biological cells cultured in an absence of albumin polypeptide. In some cases, the increase in viable cell density is at least 10%.

In yet another aspect, a method of stabilizing a protein is provided, comprising incubating the protein in the presence of a composition of any one of the preceding aspects. In some cases, the composition is present at a concentration from about 0.01% (w/w) to about 20% (w/w), from about 0.1 mg/mL to about 200 mg/mL, or at a molar ratio of about 0.1 to about 10 relative to the protein. In some cases, the protein is stabilized by at least about 80% as compared to a protein in the absence of the composition.

In yet another aspect, a composition is provided comprising: a) an albumin polypeptide; and b) arachidonic acid (C20:4) present at a molar ratio to the total amount of fatty acids in the composition of at least about 0.9%.

In yet another aspect, a method of improving a function of an albumin polypeptide is provided, the method comprising: incubating the albumin polypeptide with an amount of arachidonic acid (C20:4) sufficient to increase the molar ratio of arachidonic acid (C20:4) to the total amount of fatty acids in the composition to at least about 0.9%.

In yet another aspect, a method of improving a function of an albumin polypeptide is provided, the method comprising: a) passing a solution of the albumin polypeptide through a ceramic hydroxyapatite resin to generate a flow-through comprising the albumin polypeptide; and b) purifying the albumin polypeptide from the flow-through to yield an albumin polypeptide with an improved function. In some cases, the method further comprises, prior to a), defatting the albumin polypeptide by incubating the solution with activated charcoal, and purifying the albumin polypeptide from the activated charcoal. In some cases, the method further comprises, prior to a), incubating the solution with a chelating resin, and purifying the albumin polypeptide from the chelating resin. In some cases, the chelating resin is Diaion CR20. In some cases, the method further comprises, prior to a), incubating the albumin polypeptide with one or more fatty acids. In some cases, the one or more fatty acids are selected from the group consisting of: lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 arachidonic acid (C20:4), docosatetraenoic acid (C22:4 ω-6), and docosahexaenoic acid (C22:6 ω-3). In some cases, the one or more fatty acids consist of: lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 arachidonic acid (C20:4), docosatetraenoic acid (C22:4 ω-6), and docosahexaenoic acid (C22:6 ω-3). In some cases, the one or more fatty acids consist of: lauric acid (C12:0), myristic acid (C14:0), palmitic acid (C16:0), palmitoleic acid (C16:1), stearic acid (C18:0), oleic acid (C18:1ω-9), linoleic acid (C18:2), and eicosadienoic acid (C20:2 ω-6). In some cases, the one or more fatty acids consist of: lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 bishomo-γ-linolenic acid (C20:3 ω-6), and arachidonic acid (C20:4).

In another aspect, a composition is provided comprising: an amount of recombinant albumin polypeptide and one or more fatty acids in a molar ratio effective to promote an increase in viable cell density by at least 35% of induced pluripotent stem (iPS) cells upon culturing the iPS cells in the composition for a duration of 4 days, as compared to a composition lacking the recombinant albumin polypeptide. In another aspect, a composition is provided comprising: an amount of recombinant albumin polypeptide and one or more fatty acids in a molar ratio effective to promote an increase in viable cell density by at least 35% of mesenchymal stem cells (MSCs) upon culturing the MSCs in the composition for a duration of 5 days, as compared to a composition lacking the recombinant albumin polypeptide. In another aspect, a composition is provided comprising: an amount of recombinant albumin polypeptide and one or more fatty acids in a molar ratio effective to promote an increase in viable cell density by at least 80% of T-cells upon culturing the T-cells are cultured in the composition for a duration of 6 days, as compared to a composition lacking the recombinant albumin polypeptide. In another aspect, a composition is provided comprising: an amount of albumin polypeptide and one or more fatty acids in a molar ratio effective to promote an increase in protein stabilization by at least about 80% upon incubating the protein in the composition for a duration of about 3000 seconds to about 6000 seconds, as compared to a composition lacking the albumin polypeptide. In some cases, the composition is substantially free of growth factors.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
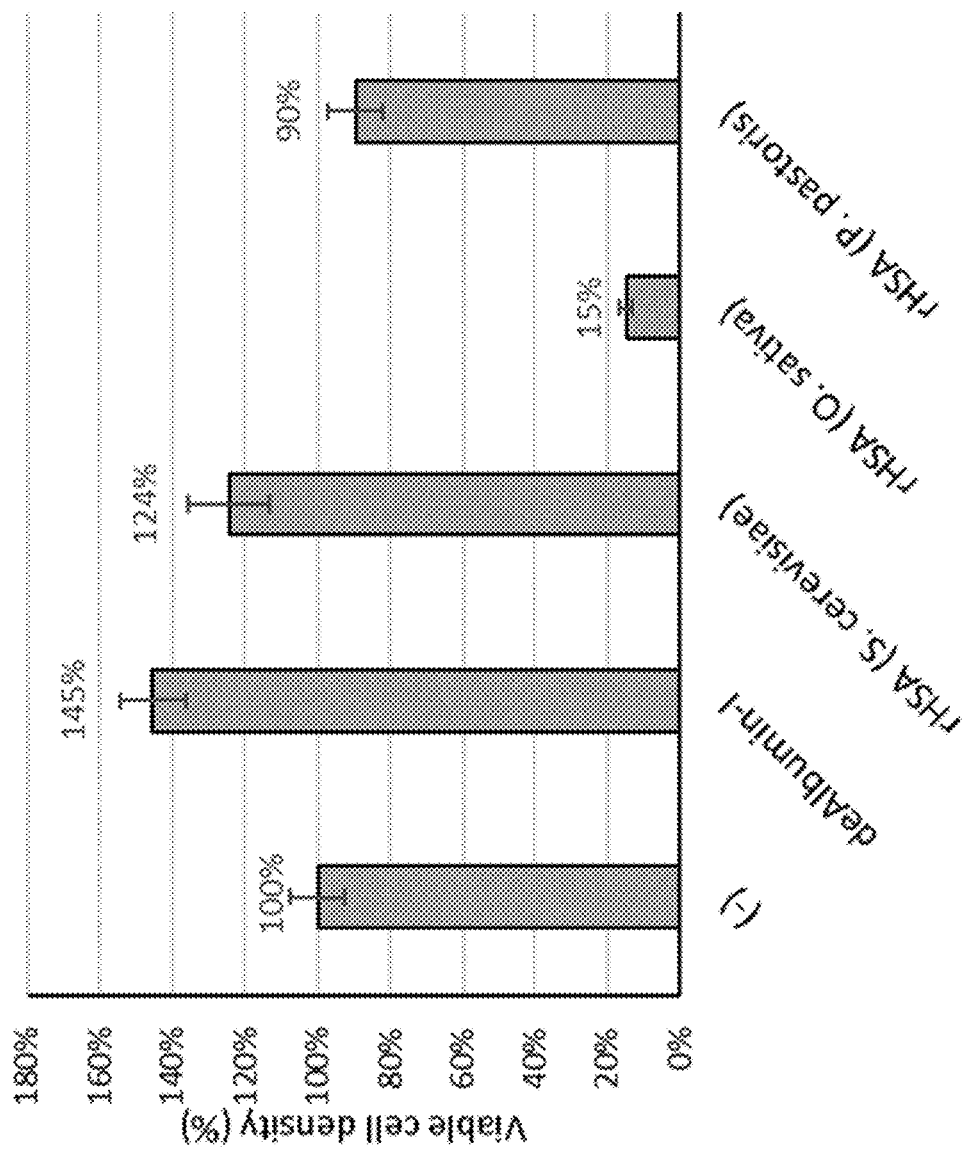
FIG. 1 depicts a non-limiting example of viable cell density of induced pluripotent stem (iPS) cells grown in E8 media supplemented with various albumins according to embodiments of the disclosure.

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

As used in the specification and claims, the singular form "a", "an" and "the" include plural references unless the context clearly dictates otherwise. For example, the term "a cell" includes a plurality of cells, including mixtures thereof.

As used herein, the term "about" a number refers to that number plus or minus 10% of that number. The term "about" a range refers to that range minus 10% of its lowest value and plus 10% of its greatest value.

The terms "albumin" and "albumin polypeptide" are used interchangeably herein and generally refer to any protein or polypeptide that is a member of, is related to, is a variant of, is a fragment of, is a truncate of, and/or is derived from the albumin family of proteins. An "albumin" or "albumin polypeptide" as used herein may be a full-length albumin protein. An "albumin" or "albumin polypeptide" as used herein may be a wild-type albumin protein. An "albumin" or "albumin polypeptide" as used herein may be a variant of a wild-type albumin protein. For example, the albumin or albumin polypeptide may comprise one or more variations relative to a wild-type albumin protein. The one or more variations may be one or more mutations. The one or more mutations may be one or more insertions, one or more deletions, and/or one or more substitutions, relative to a wild-type albumin protein. An "albumin" or "albumin polypeptide" as used herein may be a truncated form of an albumin protein. For example, the albumin or albumin polypeptide may comprise a truncation at the C-terminus, at the N-terminus, and/or an internal truncation relative to a wild-type albumin protein. An "albumin" or "albumin polypeptide" as used herein may be a fragment of an albumin protein. The albumin polypeptide may be derived from any source. In some embodiments, the albumin polypeptide is derived from blood (e.g., whole blood, plasma, serum). In some embodiments, the albumin polypeptide is recombinant albumin. The recombinant albumin may be produced in a host cell (e.g., yeast, bacteria, plant, mammalian cells, etc.).

An "albumin" or "albumin polypeptide" as used herein may comprise an amino acid sequence having at least about 50% sequence identity to a wild-type albumin protein. For example, an "albumin" or "albumin polypeptide" as used herein may comprise an amino acid sequence having at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%, sequence identity with a wild-type albumin protein.

In some embodiments, the albumin polypeptide is a serum albumin or a blood albumin. The serum albumin can be from any species. In some cases, the serum albumin is derived from a vertebrate animal. In some embodiments, the serum albumin is human serum albumin. In some embodiments, the serum albumin is bovine serum albumin. In some embodiments, the serum albumin is derived from blood.

In some cases, the albumin is a wild-type human serum albumin. In some embodiments, an "albumin" or "albumin polypeptide" as used herein comprises an amino acid sequence according to SEQ ID NO: 1 below:

(SEQ ID NO: 1)
MKWVTFISLLFLFSSAYSRGVFRRDAHKSEVAHRFKDLGEENFKALVLIA

FAQYLQQCPFEDHVKLVNEVTEFAKTCVADESAENCDKSLHTLFGDKLCT

VATLRETYGEMADCCAKQEPERNECFLQHKDDNPNLPRLVRPEVDVMCTA

FHDNEETFLKKYLYEIARRHPYFYAPELLFFAKRYKAAFTECCQAADKAA

CLLPKLDELRDEGKASSAKQRLKCASLQKFGERAFKAWAVARLSQRFPKA

EFAEVSKLVTDLTKVHTECCHGDLLECADDRADLAKYICENQDSISSKLK

ECCEKPLLEKSHCIAEVENDEMPADLPSLAADFVESKDVCKNYAEAKDVF

LGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKC

CTESLVNRRPCFSALEVDETYVPKEFNAETFTFHADICTLSEKERQIKKQ

TALVELVKHKPKATKEQLKAVMDDFAAFVEKCCKADDKETCFAEEGKKLV

AASQAALGL.

In some embodiments, the albumin polypeptide comprises an amino acid sequence having at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%, sequence identity with SEQ ID NO: 1.

In some embodiments, the albumin polypeptide is bovine serum albumin. In some embodiments, the albumin polypeptide comprises an amino acid sequence according to SEQ ID NO: 2 below:

(SEQ ID NO: 2)
MKWVTFISLLLLFSSAYSRGVFRRDTHKSEIAHRFKDLGEEHFKGLVLIA

FSQYLQQCPFDEHVKLVNELTEFAKTCVADESHAGCEKSLHTLFGDELCK

VASLRETYGDMADCCEKQEPERNECFLSHKDDSPDLPKLKPDPNTLCDEF

KADEKKFWGKYLYEIARRHPYFYAPELLYYANKYNGVFQECCQAEDKGAC

LLPKIETMREKVLASSARQRLRCASIQKFGERALKAWSVARLSQKFPKAE

FVEVTKLVTDLTKVHKECCHGDLLECADDRADLAKYICDNQDTISSKLKE

CCDKPLLEKSHCIAEVEKDAIPENLPPLTADFAEDKDVCKNYQEAKDAFL

GSFLYEYSRRHPEYAVSVLLRLAKEYEATLEECCAKDDPHACYSTVFDKL

KHLVDEPQNLIKQNCDQFEKLGEYGFQNALIVRYTRKVPQVSTPTLVEVS

RSLGKVGTRCCTKPESERMPCTEDYLSLILNRLCVLHEKTPVSEKVTKCC

-continued

TESLVNRRPCFSALTPDETYVPKAFDEKLFTFHADICTLPDTEKQIKKQT

ALVELLKHKPKATEEQLKTVMENFVAFVDKCCAADDKEACFAVEGPKLVV

STQTALA.

In some embodiments, the albumin polypeptide comprises an amino acid sequence having at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%, sequence identity with SEQ ID NO: 2.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, *Proc. Natl. Acad. Sci. USA,* 87:2264-2268 (1990) and as discussed in Altschul, et al., *J. Mol. Biol.,* 215:403-410 (1990); Karlin And Altschul, *Proc. Natl. Acad. Sci. USA,* 90:5873-5877 (1993); and Altschul et al., *Nucleic Acids Res.,* 25:3389-3402 (1997). The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, *Computers and Chemistry* 17:149-163 (1993). Ranges of desired degrees of sequence identity are approximately 50% to 100% and integer values therebetween. In general, this disclosure encompasses sequences with at least 50%, at least 55%, at least 60%, at least 65%, at least 70%, at least 75%, at least 80%, at least 85%, at least 90%, at least 95%, or at least 98% sequence identity with any sequence provided herein.

The term "fatty acid" as used herein generally refers to a carboxylic acid with an aliphatic chain which can be either saturated or unsaturated. The fatty acid can be a short-chain fatty acid, a medium-chain fatty acid, a long-chain fatty acid, or a very long-chain fatty acid. A short-chain fatty acid may be a fatty acid having an aliphatic tail of five or fewer carbons. A medium-chain fatty acid may be a fatty acid having an aliphatic tail of 6 to 12 carbons. A long-chain fatty acid may be a fatty acid having an aliphatic tail of 13 to 21 carbons. A very long-chain fatty acid may be a fatty acid having an aliphatic tail of 22 or more carbons. Generally, the fatty acids described herein are referred to by their trivial (or common) names and/or by lipid numbers. Lipid numbers as used herein take the form C:D, where C is the number of carbon atoms in the fatty acid and D is the number of double bonds in the fatty acid.

A fatty acid may be a "saturated fatty acid" meaning a fatty acid that has no C═C double bonds. Non-limiting examples of saturated fatty acids include: propionic acid (C3:0), butyric acid (C4:0), valeric acid (C5:0), caproic acid (C6:0), enanthic acid (C7:0), caprylic acid (C8:0), pelargonic acid (C9:0), capric acid (C10:0), undecylic acid (C11:0), lauric acid (C12:0), tridecylic acid (C13:0), myristic acid (C14:0), pentadecylic acid (C15:0), palmitic acid (C16:0), margaric acid (C17:0), stearic acid (C18:0), nonadecylic acid (C19:0), arachidic acid (C20:0), heneicosylic acid (C21:0), behenic acid (C22:0), tricosylic acid (C23:0), lignoceric acid (C24:0), pentacosylic acid (C25:0), cerotic acid (C26:0), carboceric acid (C27:0), montanic acid (C28:0), nonacosylic acid (C29:0), melissic acid (C30:0), hentriacontylic acid (C31:0), lacceroic acid (C32:0), psyllic acid (C33:0), geddic acid (C34:0), ceroplastic acid (C35:0), hexatriacontylic acid (C36:0), heptatriacontylic acid (C37:0), octatriacontylic acid (C38:0), nonatriacontylic acid (C39:0), and tetracontylic acid (C40:0).

A fatty acid may be an "unsaturated fatty acid" meaning a fatty acid that has one or more C═C double bonds. Unsaturated fatty acids may be in either the cis or the trans configuration. Non-limiting examples of unsaturated fatty acids include: octenoic acid (C8:1), decenoic acid (C10:1), decadienoic acid (C10:2), lauroleic acid (C12:1), laurolinoleic acid (C12:2), myristovaccenic acid (C14:1), myristolinoleic acid (C14:2), myristolinolenic acid (C14:3), palmitolinolenic acid (C16:3), palmitidonic acid (C16:4), α-linolenic acid (C18:3), stearidonic acid (C18:4), dihomo-α-linolenic acid (C20:3), eicosatetraenoic acid (C20:4), eicosapentaenoic acid (C20:5), clupanodonic acid (C22:5), docosahexaenoic acid (C22:6), 9,12,15,18,21-tetracosapentaenoic acid (C24:5), 6,9,12,15,18,21-tetracosahexaenoic acid (C24:6), myristoleic acid (C14:1), palmitovaccenic acid (C16:1), α-eleostearic acid (C18:3), β-eleostearic acid (trans-C18:3), punicic acid (C18:3), 7,10,13-octadecatrienoic acid (C18:3), 9,12,15-eicosatrienoic acid (C20:3), β-eicosatetraenoic acid (C20:4), 8-tetradecenoic acid (C14:1), 12-octadecenoic acid (C18:1), linoleic acid (C18:2), linolelaidic acid (trans-C18:2), γ-linolenic acid (C18:3), calendic acid (C18:3), pinolenic acid (C18:3), dihomo-linoleic acid (C20:2), dihomo-γ-linolenic acid (C20:3), arachidonic acid (C20:4), adrenic acid (C22:4), osbond acid (C22:5), palmitoleic acid (C16:1), vaccenic acid (C18:1), rumenic acid (C18:2), paullinic acid (C20:1), 7,10,13-eicosatrienoic acid (C20:3), oleic acid (C18:1), elaidic acid (trans-C18:1), gondoic acid (C20:1), erucic acid (C22:1), nervonic acid (C24:1), 8,11-eicosadienoic acid (C20:2), mead acid (C20:3), sapienic acid (C16:1), gadoleic acid (C20:1), 4-hexadecenoic acid (C16:1), petroselinic acid (C18:1), and 8-eicosenoic acid (C20:1).

The term "molar ratio" as used herein generally refers to the number of moles of one substance relative to the number of moles of another substance. For example, the compositions provided herein may be described in terms of molar ratio of a fatty acid to an albumin polypeptide (meaning the number of moles of fatty acid relative to the number of moles of the albumin polypeptide).

The term "substantially free", as used herein, generally refers to a composition that is lacking the specified component(s), or contains only trace amounts of the specified component(s). For example, a composition that is substantially free of a specific fatty acid may be lacking the fatty acid in the composition, or may contain only trace amounts of the fatty acid in the composition. In some embodiments, the term "substantially free" may refer to compositions that have a level of a specified component that is below the level of detection by mass spectrometry. The term "substantially free" may also refer to, e.g., a composition containing the specified component(s) at a molar ratio to the albumin polypeptide being less than 0.00005, less than 0.00001, less than 0.000005, less than 0.000001, or less than 0.0000005.

The term "formulated" when used in relation to an albumin polypeptide as described herein generally refers to an albumin polypeptide that has undergone one or more processing steps such as a defatting step, a fat formulating step, and/or a purification step.

The term "basal medium" and plural forms thereof (e.g., "basal media"), as used herein, generally refer to any medium which is capable of supporting the growth of cells (e.g., mammalian cells). The basal medium supplies standard inorganic salts, such as zinc, iron, magnesium, calcium and potassium, as well as trace elements, vitamins, an energy source, a buffer system, and/or essential amino acids. Examples of basal media include, but are not limited to, Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (SAFC Biosciences), and Iscove's Modified Dulbecco's Medium. Basal media can be supplemented with various factors (e.g., one or more of the albumin compositions described herein) to improve the growth and/or viability of cells cultured therein.

As used herein, the term "cell culture medium" and plural forms thereof (e.g., "cell culture media") generally refer to any nutritive solution for the maintenance, growth, propagation, and/or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. Cell culture medium may comprise one or more of the albumin compositions described herein.

The term "defatted" when used in reference to an albumin polypeptide described herein generally refers to an albumin polypeptide composition that has undergone a process of "defatting" to remove fatty acids. In some cases, a defatted albumin polypeptide is a "fatty acid free" or a "reduced fatty acid" composition, meaning a composition comprising about 1% or less of fatty acids. A "defatting process" as used herein may refer to any method employed to obtain a defatted albumin polypeptide, including, but not limited to, charcoal treatment, the use of resin columns, and the like.

Disclosed herein are albumin compositions having defined fatty acid profiles and methods of using the same. The albumin compositions described herein are suitable for use in cell culture methods, protein stabilization methods, amongst others. The albumin compositions described herein may improve the viability of and/or promote the growth of cells (e.g., mammalian cells) when the cells are cultured in a medium containing the albumin compositions. The albumin compositions described herein may improve the stability of a biologic when the biologic is in the presence of the albumin compositions. Further provided herein are methods of formulating albumin compositions having defined fatty acid profiles as described herein.

Albumin Compositions

In one aspect, the disclosure provides a composition comprising: a) an albumin polypeptide; b) one or more fatty acids having less than 18 carbon atoms present at a molar ratio to the albumin polypeptide ranging from about 0.02 to about 0.4; and c) one or more fatty acids having 18 carbon atoms or more present at a molar ratio to the albumin polypeptide ranging from about 0.03 to about 0.6.

The one or more fatty acids having less than 18 carbon atoms may include one or more fatty acids selected from the group consisting of: propionic acid (C3:0), butyric acid (C4:0), valeric acid (C5:0), caproic acid (C6:0), enanthic acid (C7:0), caprylic acid (C8:0), pelargonic acid (C9:0), capric acid (C10:0), undecylic acid (C11:0), lauric acid (C12:0), tridecylic acid (C13:0), myristic acid (C14:0), pentadecanoic acid (C15:0), palmitic acid (C16:0), margaric acid (C17:0), octenoic acid (C8:1), decenoic acid (C10:1), decadienoic acid (C10:2), lauroleic acid (C12:1), laurolinoleic acid (C12:2), myristovaccenic acid (C14:1), myristolinoleic acid (C14:2), myristolinolenic acid (C14:3), palmitolinolenic acid (C16:3), and palmitidonic acid (C16:4).

In some cases, the one or more fatty acids having less than 18 carbon atoms comprises one or more fatty acids selected from the group consisting of: lauric acid (C12:0), myristic acid (C14:0), palmitic acid (C16:0), and palmitoleic acid (C16:1). In some cases, the one or more fatty acids having less than 18 carbon atoms consists of lauric acid (C12:0), myristic acid (C14:0), palmitic acid (C16:0), and palmitoleic acid (C16:1).

The one or more fatty acids having less than 18 carbon atoms may be present in the composition at a molar ratio to the albumin polypeptide ranging from about 0.02 to about 0.4. For example, the one or more fatty acids having less than 18 carbon atoms may be present in the composition at a molar ratio to the albumin polypeptide of about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, or about 0.40. In some cases, the one or more fatty acids having less than 18 carbons is bound to the albumin polypeptide.

The one or more fatty acids having 18 carbon atoms or more may include one or more fatty acids selected from the group consisting of: stearic acid (C18:0), nonadecylic acid (C19:0), arachidic acid (C20:0), heneicosylic acid (C21:0), behenic acid (C22:0), tricosylic acid (C23:0), lignoceric acid (C24:0), pentacosylic acid (C25:0), cerotic acid (C26:0), carboceric acid (C27:0), montanic acid (C28:0), nonacosylic acid (C29:0), melissic acid (C30:0), hentriacontylic acid (C31:0), lacceroic acid (C32:0), psyllic acid (C33:0), geddic acid (C34:0), ceroplastic acid (C35:0), hexatriacontylic acid (C36:0), heptatriacontylic acid (C37:0), octatriacontylic acid (C38:0), nonatriacontylic acid (C39:0), tetracontylic acid (C40:0), α-linolenic acid (C18:3), stearidonic acid (C18:4), dihomo-α-linolenic acid (C20:3), eicosatetraenoic acid (C20:4), eicosapentaenoic acid (C20:5), clupanodonic acid (C22:5), docosahexaenoic acid (C22:6), 9,12,15,18,21-tetracosapentaenoic acid (C24:5), 6,9,12,15,18,21-tetracosahexaenoic acid (C24:6), myristoleic acid (C14:1), palmitovaccenic acid (C16:1), α-eleostearic acid (C18:3), β-eleostearic acid (trans-C18:3), punicic acid (C18:3), 7,10,13-octadecatrienoic acid (C18:3), 9,12,15-eicosatrienoic acid (C20:3), β-eicosatetraenoic acid (C20:4), 8-tetradecenoic acid (C14:1), 12-octadecenoic acid (C18:1), linoleic acid (C18:2), linolelaidic acid (trans-C18:2), γ-linolenic acid (C18:3), calendic acid (C18:3), pinolenic acid (C18:3), dihomo-linoleic acid (C20:2), dihomo-γ-linolenic acid (C20:3), arachidonic acid (C20:4), adrenic acid (C22:4), osbond acid (C22:5), palmitoleic acid (C16:1), vaccenic acid (C18:1), rumenic acid (C18:2), paullinic acid (C20:1), 7,10,13-eicosatrienoic acid (C20:3), oleic acid (C18:1), elaidic acid (trans-C18:1), gondoic acid (C20:1), erucic acid (C22:1), nervonic acid (C24:1), 8,11-eicosadienoic acid (C20:2), mead acid (C20:3), sapienic acid (C16:1), gadoleic acid (C20:1), 4-hexadecenoic acid (C16:1), petroselinic acid (C18:1), and 8-eicosenoic acid (C20:1).

In some cases, the one or more fatty acids having 18 carbon atoms or more comprises one or more fatty acids selected from the group consisting of: stearic acid (C18:0), oleic acid (C18:1ω-9), linoleic acid (C18:2), and eicosadienoic acid (C20:2 ω-6). In some cases, the one or more fatty acids having 18 carbon atoms or more consists of stearic acid (C18:0), oleic acid (C18:1ω-9), linoleic acid (C18:2), and eicosadienoic acid (C20:2 ω-6). In some cases, the one or more fatty acids having 18 carbon atoms or more further comprises one or more fatty acids selected from the group consisting of: bishomo-γ-linolenic acid (C20:3 arachidonic acid (C20:4), docosatetraenoic acid (C22:4 ω-6), and docosahexaenoic acid (C22:6 ω-3).

The one or more fatty acids having 18 carbon atoms or more may be present in the composition at a molar ratio to the albumin polypeptide ranging from about 0.03 to about 0.6. For example, the one or more fatty acids having 18 carbon atoms or more may be present in the composition at a molar ratio to the albumin polypeptide of about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, or about 0.60. In some cases, the one or more fatty acids having 18 carbons or more is bound to the albumin polypeptide.

In a particular aspect, the one or more fatty acids having less than 18 carbon atoms consists of lauric acid (C12:0), myristic acid (C14:0), palmitic acid (16:0), and palmitoleic acid (C16:1); and the one or more fatty acids having 18 carbon atoms or more consists of stearic acid (C18:0), oleic acid (C18:1ω-9), linoleic acid (C18:2), eicosadienoic acid (C20:2 ω-6), bishomo-γ-linolenic acid (C20:3 arachidonic acid (C20:4), docosatetraenoic acid (C22:4 ω-6), and docosahexaenoic acid (C22:6 ω-3).

In a particular aspect, the one or more fatty acids having less than 18 carbon atoms consists of lauric acid (C12:0), myristic acid (C14:0), palmitic acid (C16:0), and palmitoleic acid (C16:1); and the one or more fatty acids having 18 carbon atoms or more consists of stearic acid (C18:0), oleic acid (C18:1ω-9), linoleic acid (C18:2), and eicosadienoic acid (C20:2 ω-6).

In a particular aspect, the one or more fatty acids having less than 18 carbon atoms consists of lauric acid (C12:0), myristic acid (C14:0), palmitic acid (C16:0), and palmitoleic acid (C16:1); and the one or more fatty acids having 18 carbon atoms or more consists of stearic acid (C18:0), oleic acid (C18:1ω-9), linoleic acid (C18:2), eicosadienoic acid (C20:2 ω-6), bishomo-γ-linolenic acid (C20:3 ω-6), and arachidonic acid (20:4).

In a particular aspect, the composition is substantially free of pentadecanoic acid (C15:0), margaric acid (C17:0), and/or heptadecenoic acid (C17:1 ω-7). In various aspects, the composition may be substantially free of one or more fatty acids selected from the group consisting of: α-linolenic acid (C18:3), γ-linolenic acid (C18:3), arachidic acid (C20:0), eicosatrienoic acid (C20:3 bishomo-γ-linolenic acid (C20:3 arachidonic acid (C20:4), eicosapentaenoic acid (C20:5 behenic acid (C22:0), docosatetraenoic acid (C22:4 docosapentaenoic acid (C22:5 ω-3), docosahexaenoic acid (C22:6 ω-3), lignoceric acid (C24:0), or cerotic acid (C26:0).

In various aspects, a total molar ratio of fatty acids (e.g., the one or more fatty acids having less than 18 carbon atoms, and the one or more fatty acids having 18 carbon atoms or more) to the albumin polypeptide is less than about 1. For example, a total molar ratio of fatty acids to the albumin polypeptide may be about 1, about 0.9, about 0.8, about 0.7, about 0.6, about 0.5, about 0.4, about 0.3, about 0.2, about 0.1, about 0.09, about 0.08, about 0.07, about 0.06, about 0.05, about 0.04, about 0.03, about 0.02, or about 0.01.

In another aspect, a composition is provided comprising: a) an albumin polypeptide; b) lauric acid (C12:0) present at a molar ratio to the albumin polypeptide ranging from about 0.001 to about 0.008; c) myristic acid (C14:0) present at a molar ratio to the albumin polypeptide ranging from about 0.001 to about 0.022; d) palmitic acid (C16:0) present at a molar ratio to the albumin polypeptide ranging from about 0.02 to about 0.3; e) palmitoleic acid (C16:1) present at a molar ratio to the albumin polypeptide ranging from about 0.002 to about 0.03; 0 stearic acid (C18:0) present at a molar ratio to the albumin polypeptide ranging from about 0.011 to about 0.2; g) oleic acid (C18:1ω-9) present at a molar ratio to the albumin polypeptide ranging from about 0.02 to about 0.3; h) linoleic acid (C18:2) present at a molar ratio to the albumin polypeptide ranging from about 0.0002 to about 0.12; and i) eicosadienoic acid (C20:2 ω-6) present at a molar ratio to the albumin polypeptide ranging from about 0.0001 to about 0.002.

In various aspects, the lauric acid (C12:0) is present at a molar ratio to the albumin polypeptide ranging from about 0.001 to about 0.008. For example, the lauric acid (C12:0) may be present at a molar ratio to the albumin polypeptide of about 0.001, about 0.002, about 0.003, about 0.004, about 0.005, about 0.006, about 0.007, or about 0.008.

In various aspects, the myristic acid (C14:0) is present at a molar ratio to the albumin polypeptide ranging from about 0.001 to about 0.022. For example, the myristic acid (C14:0) may be present at a molar ratio to the albumin polypeptide of about 0.001, about 0.002, about 0.003, about 0.004, about 0.005, about 0.006, about 0.007, about 0.008, about 0.009, about 0.010, about 0.011, about 0.012, about 0.013, about 0.014, about 0.015, about 0.016, about 0.017, about 0.018, about 0.019, about 0.020, about 0.021, or about 0.022.

In various aspects, the palmitic acid (C16:0) is present at a molar ratio to the albumin polypeptide ranging from about 0.02 to about 0.3. For example, the palmitic acid (C16:0) may be present at a molar ratio to the albumin polypeptide of about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, or about 0.30.

In various aspects, the palmitoleic acid (C16:1) is present at a molar ratio to the albumin polypeptide ranging from about 0.002 to about 0.03. For example, the palmitoleic acid (C16:1) may be present at a molar ratio to the albumin polypeptide of about 0.002, about 0.003, about 0.004, about 0.005, about 0.006, about 0.007, about 0.008, about 0.009, about 0.010, about 0.011, about 0.012, about 0.013, about 0.014, about 0.015, about 0.016, about 0.017, about 0.018, about 0.019, about 0.020, about 0.021, about 0.022, about 0.023, about 0.024, about 0.025, about 0.026, about 0.027, about 0.028, about 0.029, or about 0.030.

In various aspects, the stearic acid (C18:0) is present at a molar ratio to the albumin polypeptide ranging from about 0.011 to about 0.2. For example, the stearic acid (C18:0) may be present at a molar ratio to the albumin polypeptide of about 0.011, about 0.012, about 0.013, about 0.014, about 0.015, about 0.016, about 0.017, about 0.018, about 0.019, about 0.020, about 0.030, about 0.040, about 0.050, about 0.060, about 0.070, about 0.080, about 0.090, about 0.100, about 0.110, about 0.120, about 0.130, about 0.140, about 0.150, about 0.160, about 0.170, about 0.180, about 0.190, or about 0.200.

In various aspects, the oleic acid (C18:1ω-9) is present at a molar ratio to the albumin polypeptide ranging from about 0.02 to about 0.3. For example, the oleic acid (C18:1ω-9) may be present at a molar ratio to the albumin polypeptide of about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, or about 0.30.

In various aspects, the linoleic acid (C18:2) is present at a molar ratio to the albumin polypeptide ranging from about 0.0002 to about 0.12. For example, the linoleic acid (C18:2) may be present at a molar ratio to the albumin polypeptide of about 0.0002, about 0.0003, about 0.0004, about 0.0005, about 0.0006, about 0.0007, about 0.0008, about 0.0009, about 0.0010, about 0.0020, about 0.0030, about 0.0040, about 0.0050, about 0.0060, about 0.0070, about 0.0080, about 0.0090, about 0.0100, about 0.0200, about 0.0300, about 0.0400, about 0.0500, about 0.0600, about 0.0700, about 0.0800, about 0.0900, about 0.1000, about 0.1100, or about 0.1200.

In various aspects, the eicosadienoic acid (C20:2 ω-6) is present at a molar ratio to the albumin polypeptide ranging from about 0.0001 to about 0.002. For example, the eicosadienoic acid (C20:2 ω-6) may be present at a molar ratio to the albumin polypeptide of about 0.0001, about 0.0002, about 0.0003, about 0.0004, about 0.0005, about 0.0006, about 0.0007, about 0.0008, about 0.0009, about 0.0010, about 0.0011, about 0.0012, about 0.0013, about 0.0014, about 0.0015, about 0.0016, about 0.0017, about 0.0018, about 0.0019, or about 0.0020.

In various aspects, the composition may further comprise bishomo-γ-linolenic acid (C20:3 ω-6) present at a molar ratio to the albumin polypeptide ranging from about 0.0003 to about 0.002. For example, the bishomo-γ-linolenic acid (C20:3 ω-6) may be present at a molar ratio to the albumin polypeptide of about 0.0003, about 0.0004, about 0.0005, about 0.0006, about 0.0007, about 0.0008, about 0.0009, about 0.0010, about 0.0011, about 0.0012, about 0.0013, about 0.0014, about 0.0015, about 0.0016, about 0.0017, about 0.0018, about 0.0019, or about 0.0020.

In various aspects, the composition may further comprise arachidonic acid (C20:4) present at a molar ratio to the albumin polypeptide ranging from about 0.001 to about 0.01. For example, the arachidonic acid (C20:4) may be present at a molar ratio to the albumin polypeptide of about 0.001, about 0.002, about 0.003, about 0.004, about 0.005, about 0.006, about 0.007, about 0.008, about 0.009, or about 0.010.

In various aspects, the composition may further comprise docosatetraenoic acid (C22:4 ω-6) present at a molar ratio to the albumin polypeptide ranging from about 0.0009 to about 0.003. For example, the docosatetraenoic acid (C22:4 ω-6) may be present at a molar ratio to the albumin polypeptide of about 0.0009, about 0.0010, about 0.0011, about 0.0012, about 0.0013, about 0.0014, about 0.0015, about 0.0016, about 0.0017, about 0.0018, about 0.0019, about 0.0020, about 0.0021, about 0.0022, about 0.0023, about 0.0024, about 0.0025, about 0.0026, about 0.0027, about 0.0028, about 0.0029, or about 0.0030.

In various aspects, the composition may further comprise docosahexaenoic acid (C22:6 ω-3) present at a molar ratio to the albumin polypeptide ranging from about 0.0003 to about 0.001. For example, the docosahexaenoic acid (C22:6 ω-3) may be present at a molar ratio to the albumin polypeptide ranging of about 0.0003, about 0.0004, about 0.0005, about 0.0006, about 0.0007, about 0.0008, about 0.0009, or about 0.0010.

In various aspects, a total molar ratio of fatty acid to the albumin polypeptide is from about 0.06 to about 1. For example, the total molar ratio of fatty acid to the albumin polypeptide is about 0.06, about 0.07, about 0.08, about 0.09, or about 0.10, about 0.20, about 0.30, about 0.40, about 0.50, about 0.60, about 0.70, about 0.80, about 0.90, or about 1.00.

In various aspects, the composition is substantially free of pentadecanoic acid (C15:0), margaric acid (C17:0), heptadecenoic acid (C17:1 ω-7), α-linolenic acid (C18:3), γ-linolenic acid (C18:3), arachidic acid (C20:0), eicosatrienoic acid (C20:3 eicosapentaenoic acid (C20:5 ω-3), behenic acid (C22:0), docosapentaenoic acid (C22:5 ω-3), lignoceric acid (C24:0), and/or cerotic acid (C26:0).

In another aspect, a composition is provided comprising: a) an albumin polypeptide; and b) one or more fatty acids, wherein the composition is substantially free of one or more of pentadecanoic acid (C15:0), margaric acid (C17:0), heptadecenoic acid (C17:1 ω-7), α-linolenic acid (C18:3), γ-linolenic acid (C18:3), arachidic acid (C20:0), eicosatrienoic acid (C20:3 ω-3), eicosapentaenoic acid (C20:5 behenic acid (C22:0), docosapentaenoic acid (C22:5 ω-3), lignoceric acid (C24:0), and cerotic acid (C26:0), and wherein a total molar ratio of the one or more fatty acids to the albumin polypeptide is from about 0.05 to about 1.

In another aspect, a composition is provided comprising: a) an albumin polypeptide; and b) fatty acids, wherein the fatty acids consist of: i) lauric acid (C12:0); ii) myristic acid (C14:0); iii) palmitic acid (C16:0); iv) palmitoleic acid (C16:1); v) stearic acid (C18:0); vi) oleic acid (C18:1ω-9); vii) linoleic acid (C18:2); viii) eicosadienoic acid (C20:2 ω-6); ix) bishomo-γ-linolenic acid (C20:3 ω-6); x) arachidonic acid (C20:4); xi) docosatetraenoic acid (C22:4 ω-6); and xii) docosahexaenoic acid (C22:6 ω-3), wherein a total molar ratio of the fatty acids to the albumin polypeptide is less than about 1.

In various aspects, the lauric acid (C12:0) is present at a molar ratio to the albumin polypeptide of less than about 0.01. For example, the lauric acid (C12:0) may be present at a molar ratio to the albumin polypeptide of about 0.001, about 0.002, about 0.003, about 0.004, about 0.005, about 0.006, about 0.007, or about 0.008, or about 0.009.

In various aspects, the myristic acid (C14:0) is present at a molar ratio to the albumin polypeptide of less than about 0.05. For example, the myristic acid (C14:0) may be present at a molar ratio to the albumin polypeptide of about 0.001, about 0.002, about 0.003, about 0.004, about 0.005, about 0.006, about 0.007, about 0.008, about 0.009, about 0.010, about 0.020, about 0.030, or about 0.040.

In various aspects, the palmitic acid (C16:0) is present at a molar ratio to the albumin polypeptide of less than about 0.5. For example, the palmitic acid (C16:0) may be present at a molar ratio to the albumin polypeptide of about 0.02, about 0.03, about 0.04, about 0.05, about 0.06, about 0.07, about 0.08, about 0.09, about 0.10, about 0.20, about 0.30, or about 0.40.

In various aspects, the palmitoleic acid (C16:1) is present at a molar ratio to the albumin polypeptide of less than about 0.05. For example, the palmitoleic acid (C16:1) may be present at a molar ratio to the albumin polypeptide of about 0.002, about 0.003, about 0.004, about 0.005, about 0.006, about 0.007, about 0.008, about 0.009, about 0.010, about 0.020, about 0.030, or about 0.040.

In various aspects, the stearic acid (C18:0) is present at a molar ratio to the albumin polypeptide of less than about 0.2. For example, the stearic acid (C18:0) may be present at a molar ratio to the albumin polypeptide of about 0.011, about 0.012, about 0.013, about 0.014, about 0.015, about 0.016, about 0.017, about 0.018, about 0.019, about 0.020, about 0.030, about 0.040, about 0.050, about 0.060, about 0.070, about 0.080, about 0.090, about 0.100, about 0.110, about 0.120, about 0.130, about 0.140, about 0.150, about 0.160, about 0.170, about 0.180, or about 0.190.

In various aspects, the oleic acid (C18:1ω-9) is present at a molar ratio to the albumin polypeptide of less than about 0.5. For example, the oleic acid (C18:1ω-9) may be present at a molar ratio to the albumin polypeptide of about 0.02, about 0.03, about 0.04, about 0.05, about 0.06, about 0.07, about 0.08, about 0.09, about 0.10, about 0.20, about 0.30, or about 0.40.

In various aspects, the linoleic acid (C18:2) is present at a molar ratio to the albumin polypeptide of less than about 0.2. For example, the linoleic acid (C18:2) may be present at a molar ratio to the albumin polypeptide of about 0.0002, about 0.0003, about 0.0004, about 0.0005, about 0.0006, about 0.0007, about 0.0008, about 0.0009, about 0.0010, about 0.0020, about 0.0030, about 0.0040, about 0.0050, about 0.0060, about 0.0070, about 0.0080, about 0.0090, about 0.0100, about 0.0200, about 0.0300, about 0.0400, about 0.0500, about 0.0600, about 0.0700, about 0.0800, about 0.0900, or about 0.1000.

In various aspects, the eicosadienoic acid (C20:2 ω-6) is present at a molar ratio to the albumin polypeptide of less than about 0.005. For example, the eicosadienoic acid (C20:2 ω-6) may be present at a molar ratio to the albumin polypeptide of about 0.0001, about 0.0002, about 0.0003, about 0.0004, about 0.0005, about 0.0006, about 0.0007, about 0.0008, about 0.0009, about 0.0010, about 0.0020, about 0.0030, or about 0.0040.

In various aspects, the bishomo-γ-linolenic acid (C20:3 ω-6) is present at a molar ratio to the albumin polypeptide of less than about 0.005. For example, the bishomo-γ-linolenic acid (C20:3 ω-6) may be present at a molar ratio to the albumin polypeptide of about 0.0003, about 0.0004, about 0.0005, about 0.0006, about 0.0007, about 0.0008, about 0.0009, about 0.0010, about 0.0020, about 0.0030, or about 0.0040.

In various aspects, the arachidonic acid (C20:4) is present at a molar ratio to the albumin polypeptide of less than about 0.01. For example, the arachidonic acid (C20:4) may be present at a molar ratio to the albumin polypeptide of about 0.001, about 0.002, about 0.003, about 0.004, about 0.005, about 0.006, about 0.007, about 0.008, about 0.009, or about 0.010.

In various aspects, the docosatetraenoic acid (C22:4 ω-6) is present at a molar ratio to the albumin polypeptide of less than about 0.005. For example, the docosatetraenoic acid (C22:4 ω-6) may be present at a molar ratio to the albumin polypeptide of about 0.0010, about 0.0020, about 0.0030, or about 0.0040.

In various aspects, the docosahexaenoic acid (C22:6 ω-3) is present at a molar ratio to the albumin polypeptide of less than about 0.005. For example, the docosahexaenoic acid (22:6 ω-3) may be present at a molar ratio to the albumin polypeptide ranging of about 0.0003, about 0.0004, about 0.0005, about 0.0006, about 0.0007, about 0.0008, about 0.0009, or about 0.0010, about 0.0020, about 0.0030, or about 0.0040.

In yet another aspect, a composition is provided comprising: a) an albumin polypeptide; and b) fatty acids, wherein the fatty acids consist of: i) lauric acid (C12:0); ii) myristic acid (C14:0); iii) palmitic acid (C16:0); iv) palmitoleic acid (C16:1); v) stearic acid (C18:0); vi) oleic acid (C18:1ω-9); vii) linoleic acid (C18:2); and viii) eicosadienoic acid (C20:2 ω-6).

In various aspects, the lauric acid (C12:0) is present at a molar ratio to the albumin polypeptide of less than about 0.005. For example, the lauric acid (C12:0) may be present at a molar ratio to the albumin polypeptide of about 0.001, about 0.002, about 0.003, or about 0.004.

In various aspects, the myristic acid (C14:0) is present at a molar ratio to the albumin polypeptide of less than about 0.005. For example, the myristic acid (C14:0) may be present at a molar ratio to the albumin polypeptide of about 0.001, about 0.002, about 0.003, or about 0.004.

In various aspects, the palmitic acid (C16:0) is present at a molar ratio to the albumin polypeptide of less than about 0.05. For example, the palmitic acid (C16:0) may be present at a molar ratio to the albumin polypeptide of about 0.02, about 0.03, or about 0.04.

In various aspects, the palmitoleic acid (C16:1) is present at a molar ratio to the albumin polypeptide of less than about 0.005. For example, the palmitoleic acid (C16:1) may be present at a molar ratio to the albumin polypeptide of about 0.002, about 0.003, or about 0.004.

In various aspects, the stearic acid (C18:0) is present at a molar ratio to the albumin polypeptide of less than about 0.05. For example, the stearic acid (C18:0) may be present at a molar ratio to the albumin polypeptide of about 0.011, about 0.012, about 0.013, about 0.014, about 0.015, about 0.016, about 0.017, about 0.018, about 0.019, about 0.020, about 0.030, or about 0.040.

In various aspects, the oleic acid (C18:1ω-9) is present at a molar ratio to the albumin polypeptide of less than about 0.05. For example, the oleic acid (C18:1ω-9) may be present at a molar ratio to the albumin polypeptide of about 0.02, about 0.03, or about 0.04.

In various aspects, the linoleic acid (C18:2) is present at a molar ratio to the albumin polypeptide of less than about 0.0005. For example, the linoleic acid (C18:2) may be present at a molar ratio to the albumin polypeptide of about 0.0002, about 0.0003, or about 0.0004.

In various aspects, the eicosadienoic acid (C20:2 ω-6) is present at a molar ratio to the albumin polypeptide of less than about 0.0005. For example, the eicosadienoic acid (C20:2 ω-6) may be present at a molar ratio to the albumin polypeptide of about 0.0001, about 0.0002, about 0.0003, or about 0.0004.

In another aspect, a composition is provided comprising: a) an albumin polypeptide; and b) fatty acids, wherein the fatty acids consist of: i) lauric acid (C12:0); ii) myristic acid (C14:0); iii) palmitic acid (C16:0); iv) palmitoleic acid (C16:1); v) stearic acid (C18:0); vi) oleic acid (C18:1ω-9); vii) linoleic acid (C18:2); viii) eicosadienoic acid (C20:2 ω-6); ix) bishomo-γ-linolenic acid (C20:3 ω-6); and x) arachidonic acid (C20:4).

In various aspects, the lauric acid (C12:0) is present at a molar ratio to the albumin polypeptide of less than about 0.005. For example, the lauric acid (C12:0) may be present at a molar ratio to the albumin polypeptide of about 0.001, about 0.002, about 0.003, or about 0.004.

In various aspects, the myristic acid (C14:0) is present at a molar ratio to the albumin polypeptide of less than about 0.01. For example, the myristic acid (C14:0) may be present at a molar ratio to the albumin polypeptide of about 0.001, about 0.002, about 0.003, about 0.004, about 0.005, about 0.006, about 0.007, about 0.008, or about 0.009.

In various aspects, the palmitic acid (C16:0) is present at a molar ratio to the albumin polypeptide of less than about 0.1. For example, the palmitic acid (C16:0) may be present at a molar ratio to the albumin polypeptide of about 0.02, about 0.03, about 0.04, about 0.05, about 0.06, about 0.07, about 0.08, or about 0.09.

In various aspects, the palmitoleic acid (C16:1) is present at a molar ratio to the albumin polypeptide of less than about 0.01. For example, the palmitoleic acid (C16:1) may be present at a molar ratio to the albumin polypeptide of about 0.002, about 0.003, about 0.004, about 0.005, about 0.006, about 0.007, about 0.008, or about 0.009.

In various aspects, the stearic acid (C18:0) is present at a molar ratio to the albumin polypeptide of less than about 0.1. For example, the stearic acid (C18:0) may be present at a molar ratio to the albumin polypeptide of about 0.01, about 0.020, about 0.030, about 0.040, about 0.050, about 0.060, about 0.070, about 0.080, or about 0.090.

In various aspects, the oleic acid (C18:1ω-9) is present at a molar ratio to the albumin polypeptide of less than about 0.5. For example, the oleic acid (C18:1ω-9) may be present at a molar ratio to the albumin polypeptide of about 0.02, about 0.03, about 0.04, about 0.05, about 0.06, about 0.07, about 0.08, about 0.09, about 0.10, about 0.20, about 0.30, or about 0.40.

In various aspects, the linoleic acid (C18:2) is present at a molar ratio to the albumin polypeptide of less than about 0.05. For example, the linoleic acid (C18:2) may be present at a molar ratio to the albumin polypeptide of about 0.0002, about 0.0003, about 0.0004, about 0.0005, about 0.0006, about 0.0007, about 0.0008, about 0.0009, about 0.0010, about 0.0020, about 0.0030, or about 0.0040.

In various aspects, the eicosadienoic acid (C20:2 ω-6) is present at a molar ratio to the albumin polypeptide of less than about 0.0005. For example, the eicosadienoic acid (C20:2 ω-6) may be present at a molar ratio to the albumin polypeptide of about 0.0001, about 0.0002, about 0.0003, or about 0.0004.

In various aspects, the bishomo-γ-linolenic acid (C20:3 ω-6) is present at a molar ratio to the albumin polypeptide of less than about 0.0005. For example, the bishomo-γ-linolenic acid (C20:3 ω-6) may be present at a molar ratio to the albumin polypeptide of about 0.0003 or about 0.0004.

In various aspects, the arachidonic acid (C20:4) is present at a molar ratio to the albumin polypeptide of less than about 0.005. For example, the arachidonic acid (C20:4) may be present at a molar ratio to the albumin polypeptide of about 0.001, about 0.002, about 0.003, or about 0.004.

Further provided herein are albumin compositions having an increased molar ratio of arachidonic acid (C20:4). In a particular aspect, a composition is provided comprising: a) an albumin polypeptide; and b) arachidonic acid (C20:4) present at a molar ratio to the total amount of fatty acids in the composition of at least about 0.9% (e.g., at least about 1.0%, at least about 2.0%, at least about 3.0%, at least about 4.0%, at least about 5.0%, at least about 6.0%, at least about 7.0%, at least about 8.0%, at least about 9.0%, at least about 10.0%, or greater).

In some embodiments, the albumin polypeptide can be a full-length albumin polypeptide. In some embodiments, the albumin polypeptide can be a wild-type albumin polypeptide. In some cases, the wild-type albumin polypeptide is human serum albumin and has an amino acid sequence according to SEQ ID NO: 1. In some cases, the wild-type albumin polypeptide is bovine serum albumin and has an amino acid sequence according to SEQ ID NO: 2. In some embodiments, the albumin polypeptide is a variant of a wild-type albumin polypeptide. The variant albumin polypeptide may have one or more mutations (e.g., one or more insertions, one or more deletions, and/or one or more substitutions) relative to a wild-type albumin polypeptide. In some cases, the variant albumin polypeptide has one or more mutations (e.g., one or more insertions, one or more deletions, and/or one or more substitutions) relative to SEQ ID NO: 1. In some cases, the variant albumin polypeptide has one or more mutations (e.g., one or more insertions, one or more deletions, and/or one or more substitutions) relative to SEQ ID NO: 2. In some embodiments, the albumin polypeptide may be truncated (e.g., at the N-terminus, at the C-terminus, and/or an internal truncation) relative to a wild-type albumin polypeptide. In some cases, the albumin polypeptide is truncated (e.g., at the N-terminus, at the C-terminus, and/or an internal truncation) relative to SEQ ID NO: 1. In some cases, the albumin polypeptide is truncated (e.g., at the N-terminus, at the C-terminus, and/or an internal truncation) relative to SEQ ID NO: 2. In some embodiments, the albumin polypeptide may be a fragment of a wild-type polypeptide. In some cases, the albumin polypeptide may be a fragment of an albumin polypeptide having an amino acid sequence according to SEQ ID NO: 1. In some cases, the albumin polypeptide may be a fragment of an albumin polypeptide having an amino acid sequence according to SEQ ID NO: 2.

In some embodiments, the albumin polypeptide may have an amino acid sequence having at least about 50% sequence identity to the amino acid sequence of a wild-type albumin protein. For example, the albumin polypeptide may have an amino acid sequence having at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%, sequence identity with the amino acid sequence of a wild-type albumin protein. In some embodiments, the albumin polypeptide may have an amino acid sequence having at least about 50% sequence identity to SEQ ID NO: 1. For example, the albumin polypeptide may have an amino acid sequence having at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%, sequence identity to SEQ ID NO: 1. In some embodiments, the albumin polypeptide may have an amino acid sequence having at least about 50% sequence identity to SEQ ID NO: 2. For example, the albumin polypeptide may have an amino acid sequence having at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%, sequence identity to SEQ ID NO: 2.

The albumin polypeptide can be from any suitable species. In one embodiment, the albumin is from human. In another embodiment, the albumin is from bovine. In another embodiment, the albumin is from porcine. The albumin polypeptide may be derived from any source. In some embodiments, the albumin polypeptide is derived from blood (e.g., whole blood, plasma, serum). In some embodiments, the albumin polypeptide is a recombinant albumin polypeptide. The recombinant albumin may be produced in any host cell, including, but not limited to, bacteria, yeast, fungus, plants, mammalian cells, insect cells, and the like. In some embodiments, the albumin polypeptide may be recombinantly produced in bacteria. Without limitation, the bacteria may be of the species *Escherichia coli*. In some embodiments, the albumin polypeptide may be recombinantly produced in yeast. Without limitation, the yeast may be of the species *Pichia pastoris, Saccharomyces cerevisiae*, or *Kluyveromyces lactis*. In some embodiments, the albumin polypeptide may be recombinantly produced in plants. Without limitation, the plant may be of the species *Oryza sativa* (e.g., rice). In some embodiments, the albumin polypeptide may be recombinantly produced in mammalian cells. Without limitation, the mammalian cells can be CHO cells or HEK293 cells. In some embodiments, the albumin polypeptide may be a defatted albumin polypeptide (e.g., has undergone a defatting process, e.g., according to the methods described herein). In some embodiments, the albumin polypeptide is a commercially available albumin that has been defatted, e.g., according to the methods described herein. In some cases, the albumin polypeptide compositions described herein (e.g., the combination of the albumin polypeptide and the fatty acid mixture) are not found in nature (e.g., non-naturally occurring).

In some embodiments, the albumin compositions described herein may be in a liquid formulation (e.g., a solution) or a solid formulation. The albumin compositions described herein may be provided in a liquid formulation at a concentration of about 1% (w/w), about 5% (w/w), about 10% (w/w), about 15% (w/w), about 20% (w/w), or greater. The albumin compositions described herein may be provided in a buffer solution (e.g., Dulbecco's phosphate buffered saline (dPBS)). In some embodiments, the albumin compositions described herein may be in a dried form (e.g., lyophilized) which may be reconstituted (e.g., by the addition of a solution (e.g., dPBS)). The albumin compositions provided herein may be substantially free of one or more impurities. The albumin compositions provided herein may be substantially free of growth factors.

In various aspects, further provided herein are cell culture media, e.g., for culturing biological cells (e.g., mammalian cells). The cell culture media may include a basal medium and any of the albumin compositions described herein. The basal medium may be any basal medium, including, but not limited to, Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (SAFC Biosciences) and Iscove's Modified Dulbecco's Medium. It is understood that the type of basal medium selected is dependent on the type of cell to be cultured therein.

The albumin composition may be present in the cell culture media at any suitable concentration to achieve a desired result (e.g., improved growth and/or viability of cells cultured therein). In some embodiments, the albumin composition is present in the cell culture media at a concentration ranging from about 0.02% (w/w) to about 10% (w/w). For example, any of the albumin compositions described herein may be present in the cell culture media at about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), or about 10.0% (w/w).

In some embodiments, the albumin composition is present in the cell culture media at a concentration ranging from about 0.2 mg/mL to about 100 mg/mL. For example, the albumin composition may be present in the cell culture media at a concentration of about 0.2 mg/mL, about 0.5 mg/mL, about 1.0 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL.

The cell culture medium may further comprise one or more biological cells. Any type of biological cell may be cultured in the cell culture medium described herein. In some cases, the one or more biological cells are eukaryotic cells. In some cases, the eukaryotic cells are stem cells. Non-limiting examples of stem cells that may be cultured in the cell culture medium described herein include embryonic stem (ES) cells, induced pluripotent stem (iPS) cells, and mesenchymal stem cells (MSCs). In some cases, the eukaryotic cells are T cells. In some cases, the eukaryotic cells are neuronal cells.

In some embodiments, cells may exhibit increased cell viability, increased cell growth, or both, when the cells are cultured in a cell culture medium as described herein (e.g., including the albumin compositions described herein). In some embodiments, cells may exhibit an increase in viable cell density when the cells are cultured in a cell culture medium as described herein (e.g., including the albumin compositions described herein). In some cases, cells may exhibit an increase in viable cell density of at least about 10%, at least about 15%, at least about 20%, at least about 25%, at least about 30%, at least about 35%, at least about 40%, at least about 45%, or at least about 50%, when the cells are cultured in a cell culture medium as described herein (e.g., including the albumin compositions described herein). In any of the aforementioned embodiments, the increase in cell viability and/or cell growth is relative to cells cultured in the absence of the albumin compositions described herein.

In another aspect, further provided herein is a composition comprising an amount of albumin polypeptide and one or more fatty acids in a molar ratio effective to promote an increase in viable cell density by at least about 35% (e.g., at least about 40%, at least about 45%, at least about 50%, at least about 55%, at least about 60%, or greater) of induced pluripotent stem (iPS) cells upon culturing the iPS cells in the composition for a duration of 4 days, as compared to a composition lacking the albumin polypeptide. In some cases, the composition is added to a basal medium to provide a cell culture medium as described herein. In some cases, the albumin composition is provided in the cell culture medium at a concentration of about 0.2 mg/mL to about 2.0 mg/mL. In particular embodiments, the albumin composition is provided in the cell culture medium at a concentration of about 1.0 mg/mL. In some embodiments, the albumin composition is an albumin composition described in Example 2. A non-limiting example of culturing iPS cells in the albumin compositions described herein and measuring viable cell density is provided in Example 3. In some embodiments, viable cell density is measured by counting the number of viable cells in the culture. In a non-limiting example, iPS cells may be cultured in Essential 8 medium supplemented with the albumin composition at about 1 mg/mL to about 1.5 mg/mL.

In another aspect, provided herein is a composition comprising: an amount of albumin polypeptide and one or more fatty acids in a molar ratio effective to promote an increase in viable cell density by at least about 35% (e.g., at least about 40%, at least about 45%, at least about 50%, at least about 55%, at least about 60%, or greater) of mesenchymal stem cells (MSCs) upon culturing the MSCs in the composition for a duration of 5 days, as compared to a composition lacking the albumin polypeptide. In some cases, the composition is added to a basal medium to provide a cell culture medium as described herein. In some cases, the albumin composition is provided in the cell culture medium at a concentration of about 0.2 mg/mL to about 1.5 mg/mL. In some embodiments, the albumin composition is an albumin composition described in Example 4. A non-limiting example of culturing MSCs in the albumin compositions described herein and measuring viable cell density is provided in Example 5. In some embodiments, viable cell density is measured by counting the number of viable cells in the culture. In a non-limiting example, MSCs may be cultured in MSC chemically defined medium supplemented with the albumin composition at a concentration of about 0.5 mg/mL to about 1.5 mg/mL.

In another aspect, provided herein is a composition comprising: an amount of albumin polypeptide and one or more fatty acids in a molar ratio effective to promote an increase in viable cell density by at least about 80% (e.g., at least about 85%, at least about 90%, at least about 95%, at least about 98%, or greater) of T-cells upon culturing the T-cells in the composition for a duration of 6 days, as compared to a composition lacking the albumin polypeptide. In some cases, the albumin composition is added to a basal medium to provide a cell culture medium as described herein. In some cases, the albumin composition is provided in the cell culture medium at a concentration of about 0.5 mg/mL to about 100 mg/mL. In some embodiments, the albumin composition is an albumin composition described in Example 2. A non-limiting example of culturing T-cells in the albumin compositions described herein and measuring viable cell density is provided in Example 6. In some embodiments, viable cell density is measured by counting the number of viable cells in the culture. In a non-limiting example, T-cells may be cultured in T-cell chemically defined medium supplemented with the albumin composition at a concentration of about 0.5 mg/mL to about 100 mg/mL.

In some embodiments, the albumin compositions described herein may be used to increase the stability of a biologic. As used herein, the term "biologic" includes proteins (including polypeptides and peptides), antibodies (or fragments or derivatives thereof), aptamers (or fragments or derivatives thereof), viruses (or fragments or derivatives thereof), vaccines, biological cells (e.g., mammalian cells), and the like. In some cases, a biologic may exhibit increased stability when in the presence of the albumin compositions described herein. In some cases, a biologic may exhibit an increase in stability of at least about 70%, at least about 75%, at least about 80%, at least about 85%, at least about 90%, at least about 95%, or greater when in the presence of the albumin compositions described herein. In any of the aforementioned embodiments, the increase in stability is relative to a biologic in the absence of the albumin compositions described herein.

In some embodiments, the albumin composition may be present at a concentration ranging from about 0.01% (w/w) to about 20% (w/w) (e.g., when used to stabilize a biologic). For example, the albumin composition may be present at a concentration of about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), about 10.0% (w/w), about 11.0% (w/w), about 12.0% (w/w), about 13.0% (w/w), about 14.0% (w/w), about 15.0% (w/w), about 16.0% (w/w), about 17.0% (w/w), about 18.0% (w/w), about 19.0% (w/w), or about 20.0% (w/w).

In some embodiments, the albumin composition may be present at concentration ranging from about 0.1 mg/mL to about 200 mg/mL (e.g., when used to stabilize a biologic). For example, the albumin composition may be present at a concentration of about 0.1 mg/mL, about 0.5 mg/mL, about 1.0 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL.

In some embodiments, the albumin composition may be present at a molar ratio of about 0.1 to about 10 relative to the biologic. For example, the albumin composition may be present at a molar ratio of about 0.1, about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10.0 relative to the biologic.

In another aspect, provided herein is a composition comprising an amount of albumin polypeptide and one or more fatty acids in a molar ratio effective to promote an increase in protein stabilization by at least about 80% upon incubating the protein in the composition for a duration of about 3000 seconds to about 6000 seconds, as compared to a composition lacking the albumin polypeptide. In some cases, the albumin composition is present at a concentration of about 1 mg/mL to about 200 mg/mL. In some cases, the albumin composition is present at a molar ratio of about 0.1 to about 10 relative to the protein. In some embodiments, the albumin composition is an albumin composition as described in Example 8. In some cases, the protein is insulin, and the ability of the albumin composition to stabilize insulin aggregation is measured, for example, as described in Example 9.

Methods of Formulating Albumin Compositions

Further provided herein are methods of formulating the albumin compositions described herein. Generally, the methods involve one or more processing steps to remove the fatty acid composition of the albumin polypeptide (e.g., a de-fatting step), one or more processing steps to re-formulated the fatty acid composition of the albumin polypeptide (e.g., a fat formulating process step), and/or one or more processing steps to purify and/or remove impurities from the albumin polypeptide.

In some embodiments, the methods involve a de-fatting step. In some cases, the de-fatting step involves treating the albumin polypeptide with activated charcoal. In other cases, the de-fatting step involves ion exchange chromatography. In some embodiments, the de-fatting step removes all or substantially all fatty acids from the albumin polypeptide. The albumin polypeptide, after undergoing the de-fatting step, may be termed a "de-fatted" albumin polypeptide.

In some embodiments, the methods involve a fat formulating process. In some cases, the fat formulating process involves incubating the de-fatted albumin polypeptide in a desired fatty acid mixture. The fatty acid mixture may be any mixture of fatty acids suitable to achieve a desired composition and molar ratio of fatty acids. The fatty acid mixture may be any mixture of fatty acids as described herein, suitable to achieve the molar ratios and desired results as described herein. In some cases, the mixture of fatty acids comprises a mixture of one or more of the fatty acids selected from the group consisting of: lauric acid (C12:0), myristic acid (C14:0), palmitic acid (C16:0), palmitoleic acid (C16:1); stearic acid (C18:0); oleic acid (C18:1), linoleic acid (C18:2), eicosadienoic acid (C20:2), bishomo-γ-linolenic acid (C20:3), arachidonic acid (C20:4), docosatetraenoic acid (C22:4), and docosahexaenoic acid (C22:6).

In some embodiments, the methods may involve one or more steps to remove impurities from the albumin polypeptide, and/or purify the compositions described herein. In some cases, the methods may involve incubating the albumin polypeptide with a chelating resin (e.g., Diaion™ CR20).

In another aspect, a method for improving the function of an albumin polypeptide is provided, comprising a) passing a solution of the albumin polypeptide through a ceramic hydroxyapatite resin to generate a flow-through comprising the albumin polypeptide; and b) purifying the albumin polypeptide from the flow-through to yield an albumin polypeptide with an improved function. The method may further comprise, prior to a), defatting the albumin polypeptide by incubating the solution with activated charcoal, and purifying the albumin polypeptide from the activated charcoal. The method may further comprise, prior to a), incubating the solution with a chelating resin, and purifying the albumin polypeptide from the chelating resin. In some cases, the chelating resin is Diaion™ CR20. The method may further comprise, prior to a), incubating the albumin polypeptide with one or more fatty acids. In some cases, the one or more fatty acids are selected from the group consisting of: lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 arachidonic acid (C20:4), docosatetraenoic acid (C22:4 ω-6), and docosahexaenoic acid (C22:6 ω-3). In some cases, the one or more fatty acids consist of: lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 arachidonic acid (C20:4), docosatetraenoic acid (C22:4 ω-6), and docosahexaenoic acid (C22:6 ω-3). In some cases, the one or more fatty acids consist of: lauric acid (C12:0), myristic acid (C14:0), palmitic acid (C16:0), palmitoleic acid (C16:1), stearic acid (C18:0), oleic acid (C18:1ω-9), linoleic acid (C18:2), and eicosadienoic acid (C20:2 ω-6). In some cases, the one or more fatty acids consist of: lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 ω-6), and arachidonic acid (C20:4).

Methods of Use

Further provided herein are methods of using the albumin compositions provided herein. In some cases, the albumin compositions may be used to improve the viability and/or growth of cells (e.g., by adding the albumin composition to a basal medium). In some cases, the albumin compositions may be used to improve the stability of a biologic.

In one aspect, a method of increasing cell viability, cell growth, or both, is provided comprising incubating a cell in the presence of an albumin composition (e.g., in a cell culture medium) as described herein. In some cases, cells may exhibit an increase in viable cell density of at least about 10%, at least about 15%, at least about 20%, at least about 25%, at least about 30%, at least about 35%, at least about 40%, at least about 45%, or at least about 50%, when the cells are cultured in a cell culture medium as described herein (e.g., including the albumin compositions described herein). The increase in cell viability and/or cell growth may be relative to cells cultured in the absence of the albumin compositions described herein.

The cell culture media may include any basal medium and any of the albumin compositions described herein. The basal medium may be any basal medium, including, but not limited to, Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (SAFC Biosciences) and Iscove's Modified Dulbecco's Medium. It is understood that the type of basal medium selected is dependent on the type of cell to be cultured therein.

The albumin composition may be present in the cell culture media at any suitable concentration to achieve a desired result (e.g., improved growth and/or viability of cells cultured therein). In some embodiments, the albumin composition is present in the cell culture media at a concentration ranging from about 0.01% (w/w) to about 10% (w/w). For example, any of the albumin compositions described herein may be present in the cell culture media at about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), or about 10.0% (w/w).

In some embodiments, the albumin composition is present in the cell culture media at a concentration ranging from about 0.1 mg/mL to about 100 mg/mL. For example, the albumin composition may be present in the cell culture media at a concentration of about 0.1 mg/mL, about 0.5 mg/mL, about 1.0 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL.

Any type of cell may be cultured in the cell culture medium described herein. In some cases, the cell may be a eukaryotic cell. In some cases, the eukaryotic cell is a stem cell. Non-limiting examples of stem cells that may be cultured in the cell culture medium described herein include embryonic stem (ES) cells, induced pluripotent stem (iPS) cells, and mesenchymal stem cells (MSCs). In some cases, the eukaryotic cell is a T cell. In some cases, the eukaryotic cell is a neuronal cell.

Further provided herein are methods of increasing the stability of a biologic, comprising incubating the biologic in the presence of an albumin composition as described herein. In some cases, a biologic may exhibit an increase in stability of at least about 70%, at least about 75%, at least about 80%, at least about 85%, at least about 90%, at least about 95%, or greater when in the presence of the albumin compositions described herein. The increase in stability may be relative to a biologic in the absence of the albumin compositions described herein.

In some embodiments, the albumin composition may be present at a concentration ranging from about 0.01% (w/w) to about 20% (w/w) (e.g., when used to stabilize a biologic). For example, the albumin composition may be present at a concentration of about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.5% (w/w), about 1.0% (w/w), about 1.5% (w/w), about 2.0% (w/w), about 2.5% (w/w), about 3.0% (w/w), about 3.5% (w/w), about 4.0% (w/w), about 4.5% (w/w), about 5.0% (w/w), about 5.5% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), about 10.0% (w/w), about 11.0% (w/w), about 12.0% (w/w), about 13.0% (w/w), about 14.0% (w/w), about 15.0% (w/w), about 16.0% (w/w), about 17.0% (w/w), about 18.0% (w/w), about 19.0% (w/w), or about 20.0% (w/w).

In some embodiments, the albumin composition may be present at concentration ranging from about 0.1 mg/mL to about 200 mg/mL (e.g., when used to stabilize a biologic). For example, the albumin composition may be present at a concentration of about 0.1 mg/mL, about 0.5 mg/mL, about 1.0 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL.

In some embodiments, the albumin composition may be present at a molar ratio of about 0.1 to about 10 relative to the biologic. For example, the albumin composition may be present at a molar ratio of about 0.1, about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10.0 relative to the biologic.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Materials and Methods

Recombinant human serum albumins were purchased from various vendors: rHSA (*S. cerevisiae*) was from Sigma Aldrich Inc. (A6608), rHSA (*P. pastoris*) was from Sigma Aldrich (A7736), and rHSA (*O. sativa*) was from InVitria (Cellastim S, Optibumin). Plasma-derived human serum albumin, pHSA, is bought from Taiwan Blood Services Foundation (TBSF). pHSA (Dialyzed): pHSA which was dialyzed against at least 1000 fold of DPBS with laboratory centrifugal concentrator MWCO 30 kD. DPBS was from Gibco (14190250). Fatty acid-free BSA was from Sigma Aldrich (A8806).

Example 2. Preparation of Formulated Recombinant Human Serum Albumin, deAlbumin-I A 20% aqueous solution of 400 g recombinant HSA, expressed from *Pichia pastoris* and purified, was incubated with 1.5 kg chelating resin Diaion™ CR20 for 10 hours at room temperature. The resin was removed by filtration and the solution was acidified with 1 N hydrogen chloride to pH 3.5 and mixed with 134 g of activated charcoal. After 1 hour of gentle agitation, the solution was then neutralized by 1 N sodium hydroxide to pH 7.0. GC-MS confirmed more than 95% of total fatty acid removal from input recombinant HSA raw material. The slurry of rHSA and activated charcoal was separated by centrifugation and filtration with a 0.45 μm cartridge filter. The resulting solution of recombinant HSA was diluted to between 4-10% (w/w) of HSA with purified water. A fatty acid mixture, as described below in Table 1, was dissolved in ethanol and then added to the HSA solution and the final ethanol content was adjusted to 5%. The solution was stirred at room temperature for 2 hours, concentrated to 20% w/w of HAS, and diafiltrated with at least 7-fold volume of DPBS buffer to remove residual ethanol. The resulting HSA solution was passed through a column packed with 40 g of ceramic hydroxyapatite resin to yield the final product.

TABLE 1

List of fatty acids applied in the formulation of deAlbumin-I

| Fatty Acid name | (mg) |
|---|---|
| Lauric acid (C12:0) | 2.99 |
| Myristic acid (C14:0) | 14.60 |
| Palmitic acid (C16:0) | 219.00 |
| Palmitoleic acid (C16:1) | 16.30 |
| Stearic acid (C18:0) | 194.00 |
| Oleic acid (C18:1) | 241.00 |
| Linoleic acid (C18:2) | 120.00 |
| Eicosadienoic acid (C20:2) | 1.32 |
| Bishomo-γ-linolenic acid (C20:3) | 1.31 |
| Arachidonic acid (C20:4) | 6.49 |
| Docosatetraenoic acid (C22:4) | 1.42 |
| Docosahexaenoic acid (C22:6) | 1.40 |

Example 3. Performance Assay of Albumin by iPS Cell Culture

Induced pluripotent stem cells, iPS cells (GIBCO, A18945), were cultured in Essential 8 medium (GIBCO, A1517001) supplemented with each albumin at 1 mg/mL. iPS cells were seeded in $1 \times 10^5$/well in 6-well-plates coated with iMatrix-511 at 0.5 μg/cm$^2$. Medium was changed daily. After culturing for four days, the viable cell density of each group was determined by trypan blue methods.

The viable cell density data was plotted and is shown in FIG. 1. Various recombinant human serum albumins (from various manufacturers) were also assayed side by side.

Example 4. Preparation of Formulated Recombinant Human Serum Albumin, deAlbumin-II A 20% aqueous solution of 400 g recombinant HSA, expressed from *Pichia pastoris* and purified, was first acidified with 1 N hydrogen chloride to pH 3.5 and mixed with 134 g of activated charcoal. After 1 hour of gentle agitation, the solution was then neutralized by 1 N sodium hydroxide to pH 7.0. GC-MS confirmed more than 95% of total fatty acid removal from input recombinant HSA raw material. The slurry of rHSA and activated charcoal was separated by centrifugation and filtration with a 0.45 μm cartridge filter. The resulting solution of recombinant HSA was diluted to between 4-10% (w/w) of HSA with purified water. A fatty acid mixture, as described below in Table 2, was dissolved in ethanol and then added to HSA solution and the final ethanol content was adjusted to 5%. The solution was stirred at room temperature for 2 hours, concentrated to 20% w/w of HSA and diafiltrated with at least 7-fold volume of DPBS buffer to remove residual ethanol.

TABLE 2

List of fatty acids applied in the formulation of deAlbumin-II

| Fatty Acid name | (mg) |
|---|---|
| Lauric acid (C12:0) | 6.98 |
| Myristic acid (C14:0) | 34.10 |
| Palmitic acid (C16:0) | 510.00 |
| Palmitoleic acid (C16:1) | 38.00 |
| Stearic acid (C18:0) | 453.00 |

TABLE 2-continued

List of fatty acids applied in the formulation of deAlbumin-II

| Fatty Acid name | (mg) |
|---|---|
| Oleic acid (C18:1) | 562.00 |
| Linoleic acid (C18:2) | 279.00 |
| Eicosadienoic acid (C20:2) | 4.30 |
| Bishomo-γ-linolenic acid (C20:3) | 3.05 |
| Arachidonic acid (C20:4) | 15.20 |
| Docosatetraenoic acid (C22:4) | 3.31 |
| Docosahexaenoic acid (C22:6) | 3.27 |

Example 5. Performance Assay of Albumin by MSC Cell Culture

Figure 2:
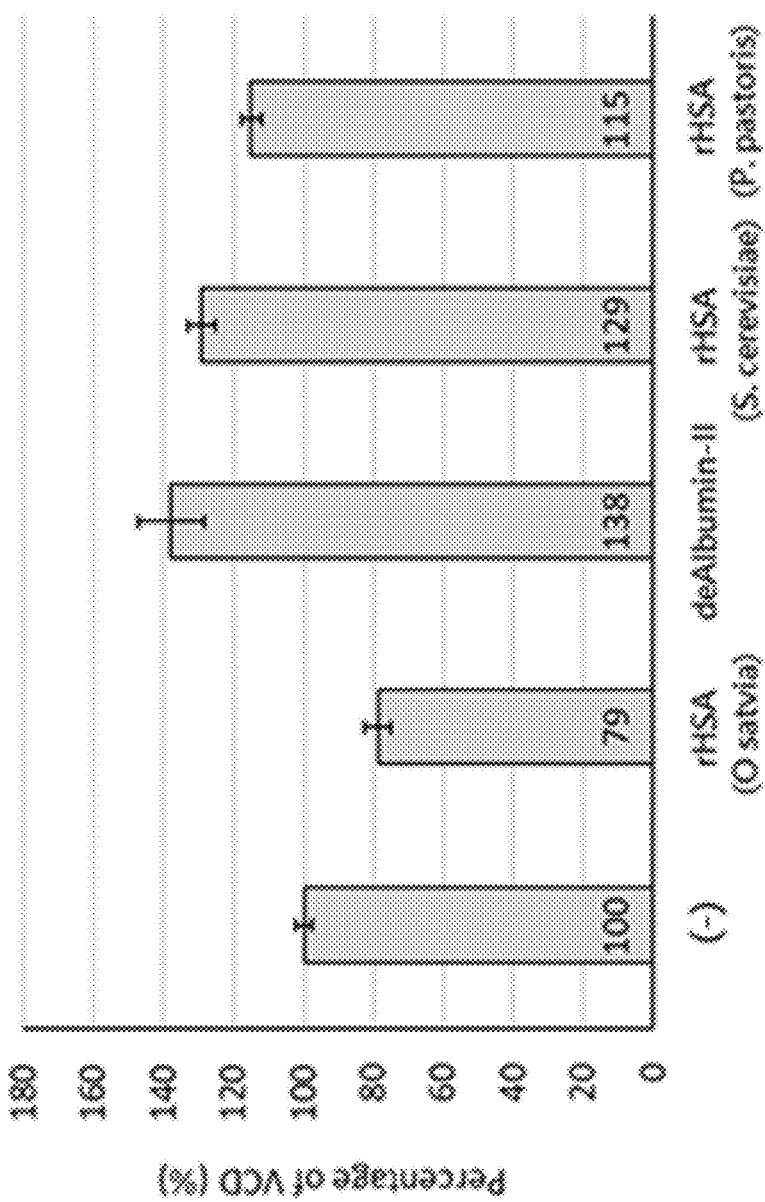
FIG. 2 depicts a non-limiting example of viable cell density of mesenchymal stem cells (MSCs) grown in chemically defined media supplemented with various albumins according to embodiments of the disclosure.

Primary Human Adipose-Derived Stem Cells, ADSC (Lonza, PT-5006) were cultured for two passages in MesenPRO RS™ medium (Gibco 12746012) until 50%-70% confluency. The ADSCs were then seeded into a 6-well-plate at $7 \times 10^3$ cell/cm$^2$ density (Day 0). To each well of cells, MSC chemically defined medium supplemented with 0.5 mg/mL of various albumins was added. The composition of the MSC chemically defined medium is described in Table 3 below. For each well, the medium was changed on Day 3. After culturing for five days, the viable cell density of each group was determined by trypan blue methods. The viable cell density data was plotted and is shown in FIG. 2. Various recombinant human serum albumins (from various manufacturers) were also assayed side by side.

TABLE 3

Composition of the MSC chemically defined medium

| Component | Concentration |
|---|---|
| Basal medium | |
| IMDM (Gibco 12240) | 1X |
| Supplements | |
| insulin | 7 mg/L |
| Apo-Transferrin | 15 mg/L |
| lipid concentrate (Gibco 11905031) | 1/100 dilution |
| monothioglycerol | 450 μM |
| bFGF | 4 μg/L |
| Fibronectin | 5 mg/L |
| 2-mercaptoethanol | 0.1 mM |

Example 6. Performance Assay of Albumin by T-Cell Culture

Figure 3:
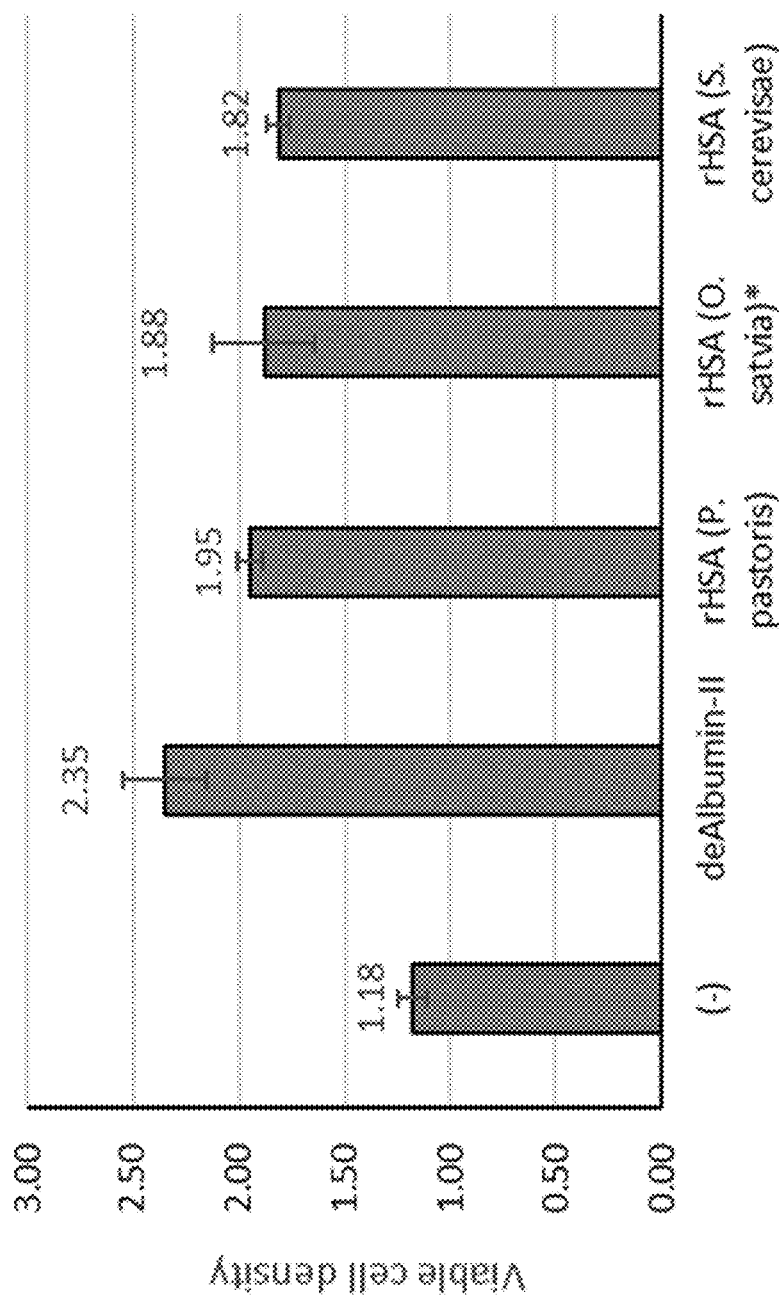
FIG. 3 depicts a non-limiting example of viable cell number of T-cells grown in chemically defined media supplemented with various albumins according to embodiments of the disclosure.

Human Peripheral Blood CD8+ T Cells (Stemcell Technologies 70027) is thawed and expanded in Immunocult™ XF media (Stemcell Technologies 10981) plus 1× Pen-Strep (Gibco 15140122) for 8 days and cryopreserved in CryoStor® CS10 (Stemcell Technologies 07930). Cells are thawed in Immunocult™ XF media and resuspended to $5 \times 10^4$ cell/mL with T-cell chemical defined media supplemented with CD3/CD28 activator (Stemcell Technologies 10971) plus each type of albumin, and then seeded into a 12 well-plate at 1 mL/well (Day 0). Each well was added with 0.5 mL of fresh media on top on Day 2, and further added with 0.75 mL of fresh media on top on Day 5. The cell number of each well was counted on Day 6. The composition of the T-cell chemically defined medium is described in Table 4 below. Results are depicted in FIG. 3.

TABLE 4

Composition of the T-cell chemically defined medium

| Components | | Concentration |
|---|---|---|
| RPMI1640 | GIBCO 21870076 | 1x |
| Insulin | GIBCO 12585014 | 5 mg/L |
| Ferric citrate | Sigma F3388 | 2 mg/L |
| Ethanolamine | Sigma E0135 | 1.22 mg/L |
| Linoleic acid | | 1 mg/L |
| Oleic acid | | 1 mg/L |
| Palmitic acid | | 1 mg/L |
| 2-mercaptoethanol | Sigma M3148 | 15 µM |
| 1-thioglycerol | Sigma M6145 | 5.41 mg/L |
| RPMI1640 nonessential amino acids | Sigma R7131 | 1x |
| RPMI1640 vitamins solution | Sigma R7256 | 1x |
| Polyamine supplement | Sigma P8483 | 0.1x |
| Cholesterol | | 13.2 mg/L |
| L-Arginine | Sigma A8094 | 2117 mg/L |
| glutamine | | 2 mM |
| IL-2 | STEMCELL 78036 | 100 IU/mL |
| Penicillin-Streptomycin | GIBCO 15140122 | 1x |

Example 7. Preparation of Formulated Bovine Serum Albumin deBSA-I

A 20% aqueous solution of 10 g BSA (Bioshop #ALB001) was first acidified with 1 N hydrogen chloride to pH 3.5 and mixed with 5 g of activated charcoal. After 1 hour of gentle agitation at 400 rpm, the solution was then neutralized by 1 N sodium hydroxide to pH 7.0. The slurry of BSA and activated charcoal was separated by filtration with a 0.2 µm filter. The resulting solution of BSA was diluted to between 4-10% (w/w) of BSA with purified water. A fatty acid mixture, as described below in Table 5, was dissolved in ethanol and then added to the BSA solution and the final ethanol content was adjusted to 5%. The solution was stirred at room temperature for 2 hours, and then concentrated to 20% w/w of BSA and exchanged with 10-fold volume of DPBS buffer three times on a 30 kDa MWCO centrifugal concentrator (sartorius #VS15T21). The formulated BSA was incubated with two-fold volume of Diaion CRB30 resin overnight and then filtered with a 0.2 µm filter to yield deBSA-I.

Example 8. Preparation of Formulated Recombinant Albumin deAlbumin-III

The same procedure was employed as in the preparation of deBSA-I described above (Example 6), except that 10 g of 20% recombinant HSA, expressed from *Pichia pastoris* and purified was used.

TABLE 5

List of fatty acids applied in the formulation of deBSA-I and deAlbumin-III

| Fatty Acid name | (mg) |
|---|---|
| Lauric acid (C12:0) | 0.21 |
| Myristic acid (C14:0) | 1.02 |
| Palmitic acid (C16:0) | 15.31 |
| Palmitoleic acid (C16:1) | 1.14 |
| Stearic acid (C18:0) | 13.59 |
| Oleic acid (C18:1) | 16.86 |

TABLE 5-continued

List of fatty acids applied in the formulation of deBSA-I and deAlbumin-III

| Fatty Acid name | (mg) |
|---|---|
| Linoleic acid (C18:2) | 8.37 |
| Eicosadienoic acid (C20:2) | 0.092 |
| Bishomo-γ-linolenic acid (C20:3) | 0.091 |
| Arachidonic acid (C20:4) | 0.454 |
| Docosatetraenoic acid (C22:4) | 0.099 |
| Docosahexaenoic acid (C22:6) | 0.10 |

Example 9. Assay of Insulin Aggregation Stabilization by Various Albumin

Figure 4:
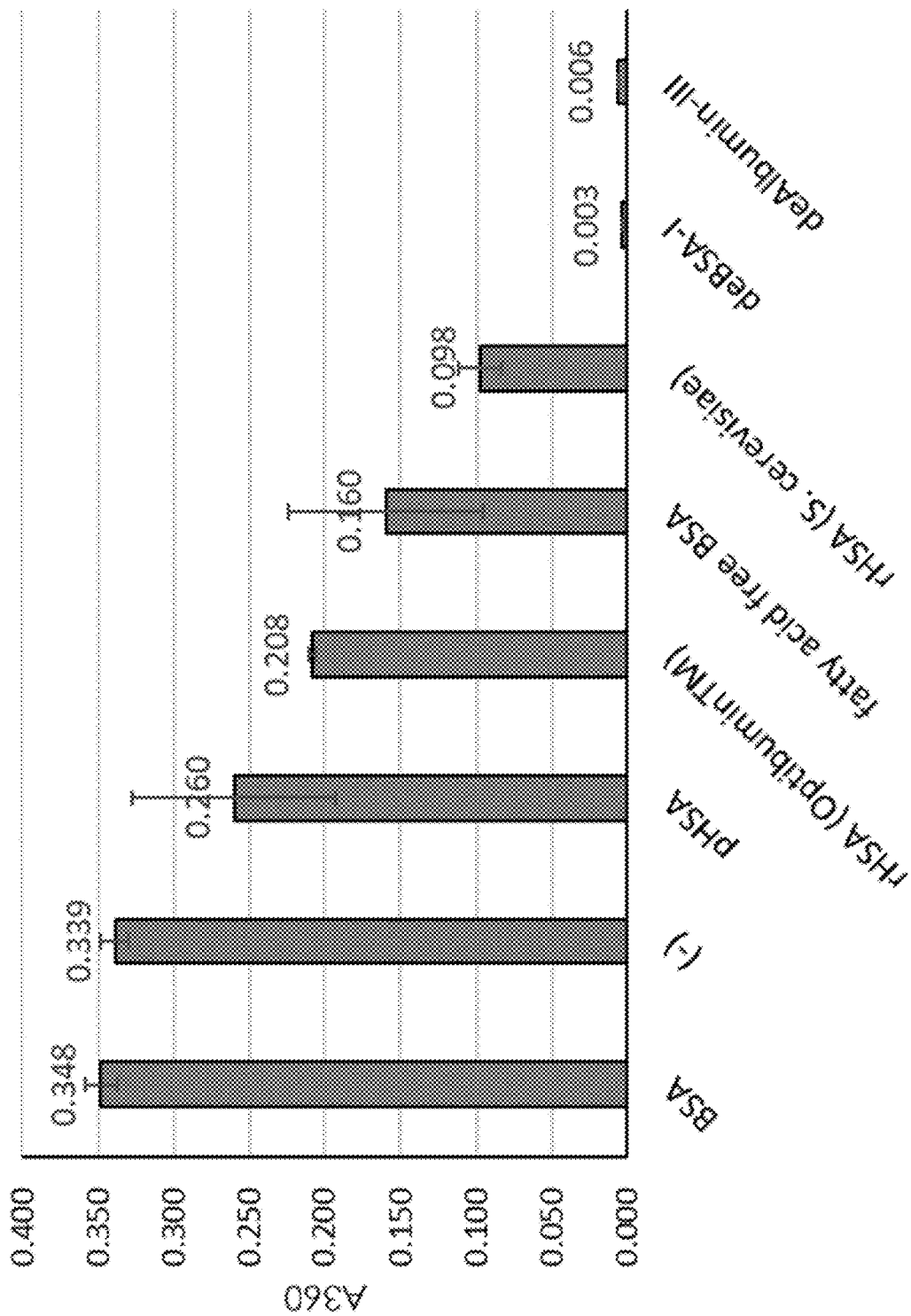
FIG. 4 depicts a non-limiting example of absorbance at 360 nm of insulin solution stabilized by various albumins according to embodiments of the disclosure.

Various albumin samples were diluted to 2 mg/mL in purified water. An assay working solution was prepared containing 60 mM of HEPES (pH=7.4), 300 mM of NaCl, 30 mM of 2-mercaptoethanol, and 0.7 mg/mL of Insulin. In a 96-well plate, 100 µL of the assay working solution was mixed with 100 µL of each albumin sample. The plate was incubated at 37° C. inside a plate reader, and the absorbance at 360 nm was measured every 30 seconds for 60 minutes. The absorbance data at 360 nm (A360) of each group was picked at the time point where the A360 of the control group (without albumin, labeled as (−)) was near 0.35. The data is depicted in FIG. 4 and the efficiency of the albumin's stabilizing effect was calculated by the equation below, and is summarized in Table 6 below.

Stabilizing Efficiency %=1−(A360 of experimental group with albumin)/(A360 of (−) group)

TABLE 6

Summary of insulin aggregation stabilization with various albumins

| Albumin | Stabilizing Efficiency |
|---|---|
| BSA | −3% |
| (−) | 0% |
| pHSA | 23% |
| rHSA (Optibumin ™) | 39% |
| fatty acid free BSA | 53% |
| rHSA (*S. cerevisiae*) | 71% |
| deBSA-I | 99% |
| deAlbumin-III | 98% |

Example 10. Fatty Acid Compositions of Various Albumins

500 µL of methanol and 25 µl of 1 N HCL was added to a 200 µL water solution of 10 mg sample of each albumin, followed by extraction with 1.5 mL of isooctane twice. The combined isooctane layers were evaporated to dryness. The residue was re-dissolved in 100 µL of 1% diisopropylethylamine in acetonitrile and reacted with 100 µL 1% pentafluorobenzyl bromide, PFB (Sigma-Aldrich, St. Louis, Mo.), in acetonitrile at room temperature for 20 minutes. After removing the solvent by evaporation, the residue was dissolved in 1500 µL isooctane and 1 µL of the fatty acid PFB esters was analyzed by Agilent 6890 Gas Chromatography (GC) coupled with Agilent 5973N Mass Spectrometry (MS) operated in negative chemical ionization (NCI) mode. Samples were injected with a pulsed (25 psi) split-less injection mode onto a Zebron ZB-1 column (15 m×0.25 mm i.d., coated with 0.1 µm 100% dimethylpolysiloxane; Phenomenex, Torrance, Calif.). Helium (0.9 mL/min was used as carrier gas. The GC oven temperature was programmed from 150° C. to 270° C. at 10° C./min, ramped to 310° C. at 20° C./min and held at 310° C. for 1 min. The injector and transfer line were kept at 250° C. and 280° C. respectively. Methane (99.99%) was used as the ionization gas with a source temperature of 150° C. Data were acquired in the selected ion monitoring (SIM) mode, monitoring the [M-H]– anions of the fatty acids. The results are depicted in Table 8.

Example 11. Altering Fatty Acid Content in Albumin Individually and Tested in MSC and T-Cell Culture deAlbumin-IV was made with the same method as shown in Example 1, with the exception that each of the fatty acids listed in Table 5 was applied to 10 g of defatted albumin during the formulation step. A list of testing albumins, 10 g of each, were formulated with individual fatty acids by the same method as in Example 1, according to the recipe below (Table 7).

TABLE 7

List of albumins formulated with individual fatty acids

| Label | Fatty Acid name | (mg) |
|---|---|---|
| Alb-1 | Laurie acid (C12:0) | 0.42 |
| Alb-2 | Myristic acid (C14:0) | 2.04 |
| Alb-3 | Palmitic acid (C16:0) | 30.62 |

TABLE 7-continued

List of albumins formulated with individual fatty acids

| Label | Fatty Acid name | (mg) |
|---|---|---|
| Alb-4 | Palmitoleic acid (C16:1) | 2.28 |
| Alb-5 | Stearic acid (C18:0) | 27.18 |
| Alb-6 | Oleic acid (C18:1) | 33.72 |
| Alb-7 | Linoleic acid (C18:2) | 16.74 |
| Alb-8 | Eicosadienoic acid (C20:2) | 0.184 |
| Alb-9 | Bishomo-γ-linolenic acid (C20:3) | 0.182 |
| Alb-10 | Arachidonic acid (C20:4) | 0.908 |
| Alb-11 | Docosatetraenoic acid (C22:4) | 0.198 |
| Alb-12 | Docosahexaenoic acid (C22:6) | 0.196 |

*Alb-6 was not tested, due to a technical issue.

Figure 5:
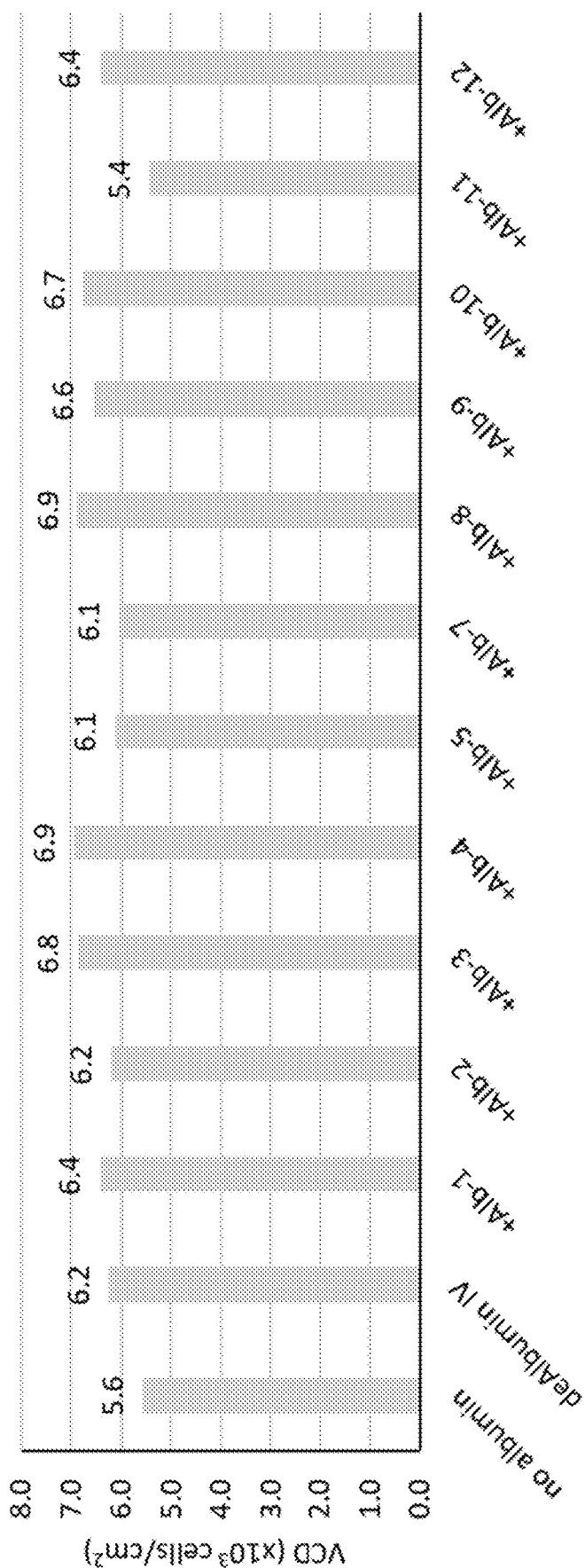
FIG. 5 depicts a non-limiting example of viable cell density of MSCs grown in chemically defined media supplemented with various albumins according to embodiments of the disclosure.
Figure 6:
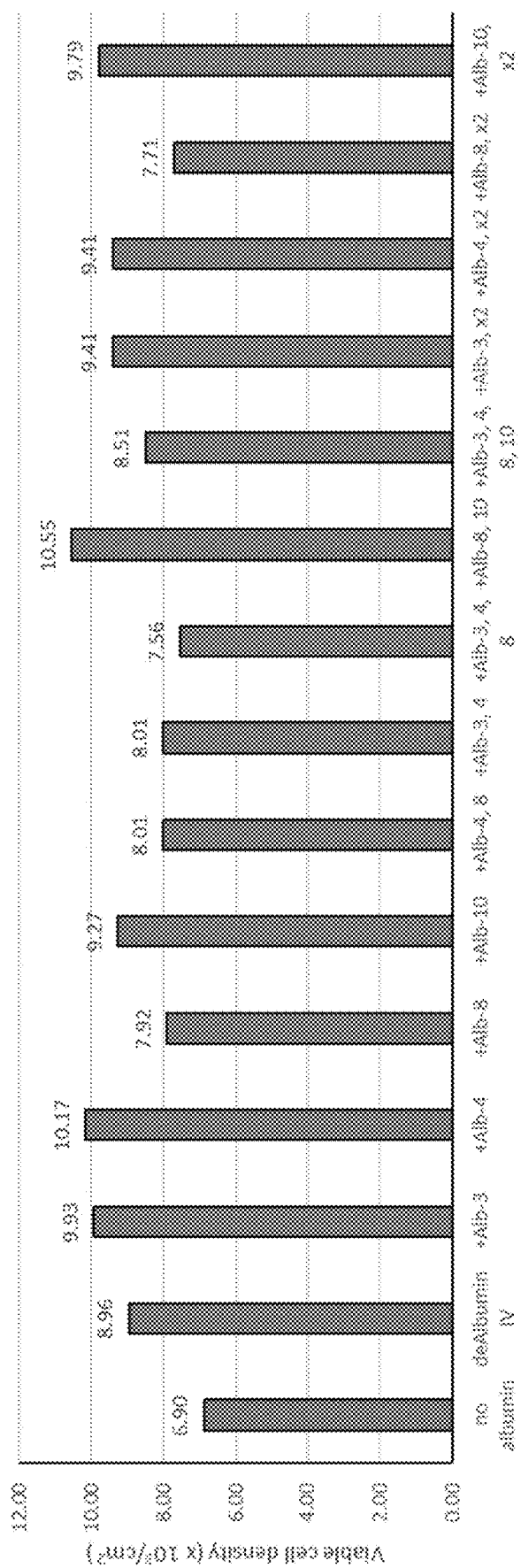
FIG. 6 depicts a non-limiting example of viable cell density of MSCs grown in chemically defined media supplemented with various albumins according to embodiments of the disclosure.
Figure 7:
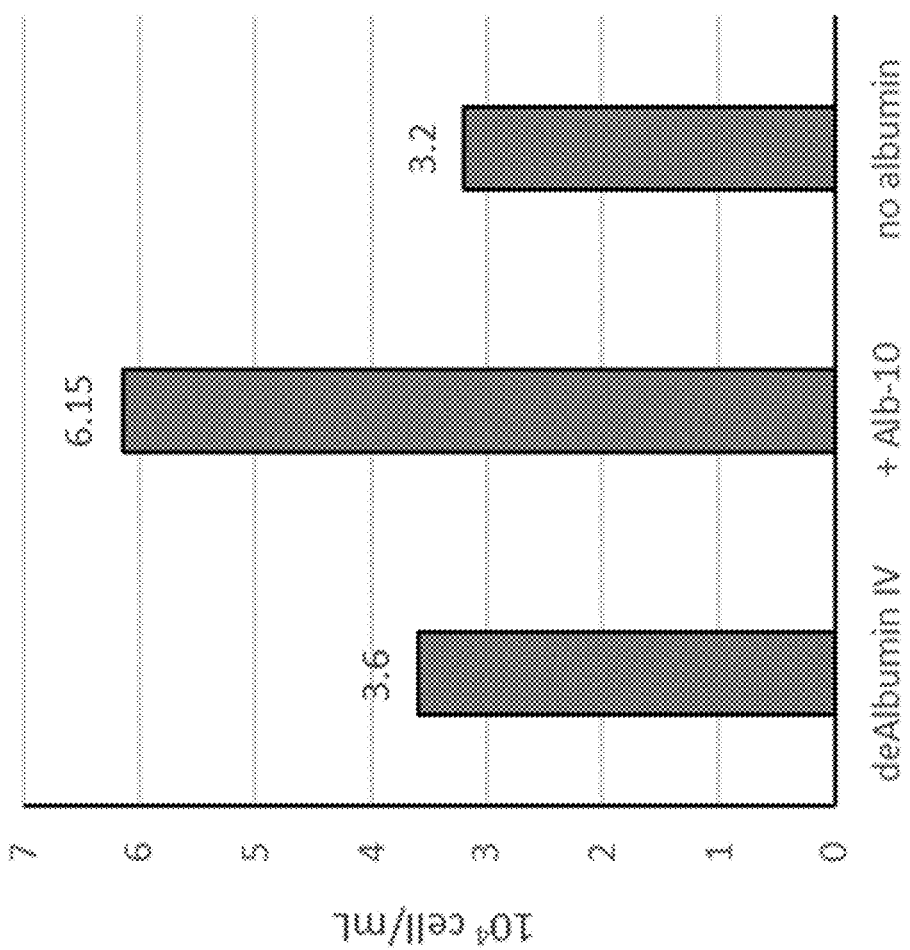
FIG. 7 depicts a non-limiting example of viable cell density of T cells grown in chemically defined media supplemented with various albumins according to embodiments of the disclosure.

0.4 mg of deAlbumin-IV was mixed with 0.1 mg of each albumin in Table 6, and the resulting mixture was subjected to MSC cell culture test as described in Example 4. Several rounds of tests on various combinations of Alb-1 to Alb-12 with deAlbumin-IV were conducted, and it was concluded that Alb-10 was helpful in the growth of T-cell and MSC among most combinations. (see FIGS. 5-7).

Figure 8:
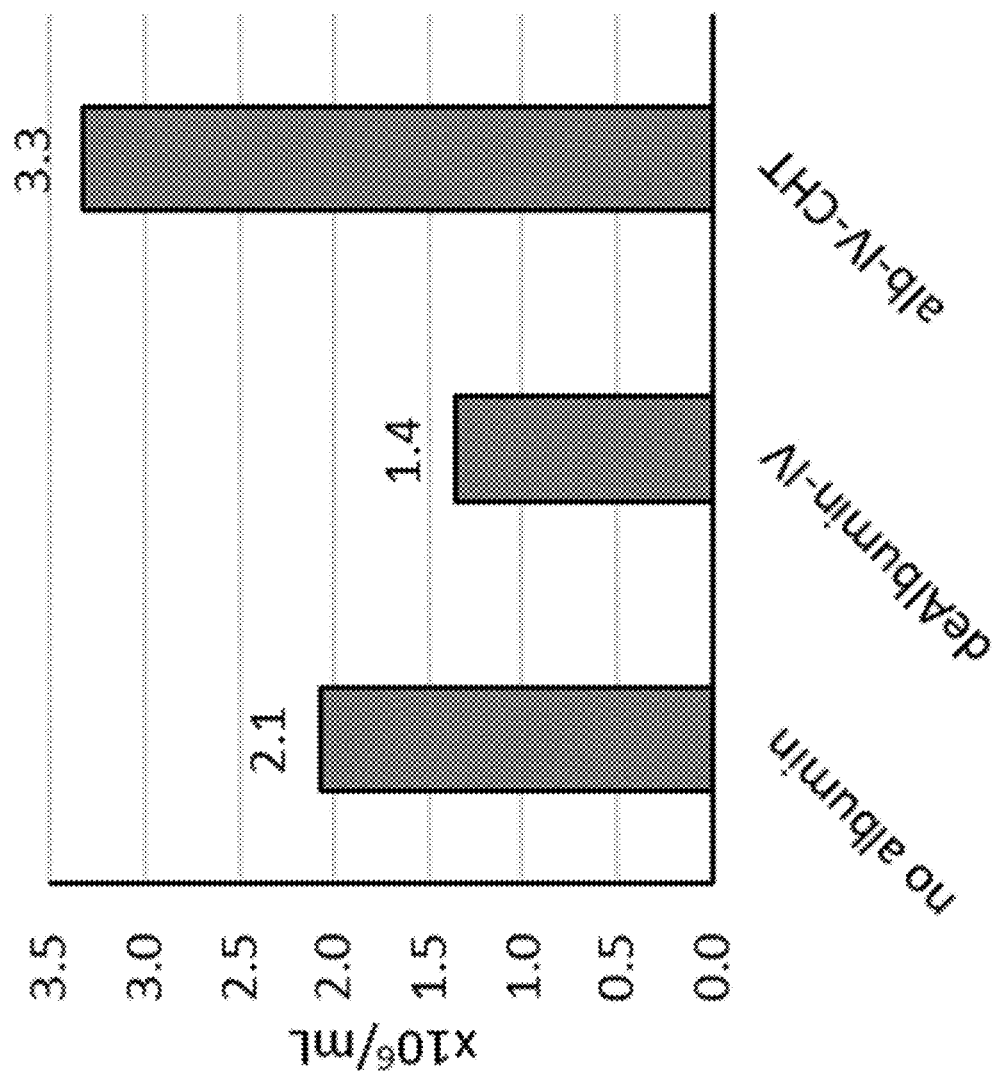
FIG. 8 depicts a non-limiting example of viable cell density of iPS cells grown in Essential 8 media supplemented with various albumins according to embodiments of the disclosure.
Figure 9:
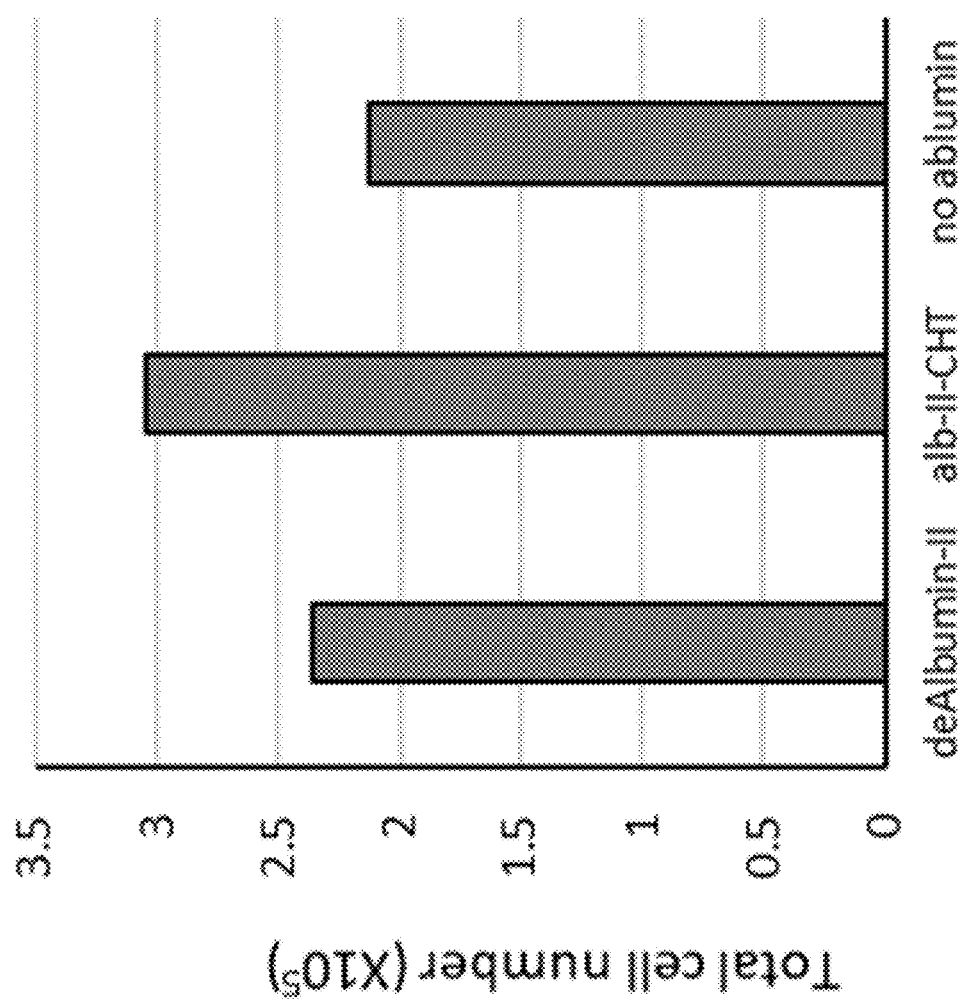
FIG. 9 depicts a non-limiting example of viable cell density of T cells grown in chemically defined media supplemented with various albumins according to embodiments of the disclosure.

Example 12. Ceramic Hydroxyapatite Improves the Cell Culture Performance of Albumin deAlbumin-IV and deAlbumin-II solutions were passed through a column packed with 10-20% w/w of ceramic hydroxyapatite resin to yield the treated albumins, labeled as alb-IV-CHT and alb-II-CHT. These albumins were tested for iPS and T-cell culture performance, respectively, by the methods described in Example 2 and Example 4. The results are shown in FIG. 8 and FIG. 9.

TABLE 8

List of fatty acid compositions of all albumin used, n.d., not detected

| Fatty Acid (molar ratio) | pHSA | pHSA (de-fatted) | rHSA (S. cere-visiae) | rHSA (P. pastoris) | rHSA (O. sativa) Cella-stim | rHSA (O. sativa)* Cella-stim S | de-Albu-min-I | de-Albu-min-II | rHSA (Opti-bumin) | de-Albu-min-III | BSA | deBSA-I | BSA-Free | de-Albu-min-IV |
|---|---|---|---|---|---|---|---|---|---|---|---|---|---|---|
| Lauric acid (C12:0) | 0.0099 | n.d. | 0.0088 | 0.0145 | 0.0013 | 0.0039 | 0.0022 | 0.0076 | n.d. | 0.0010 | 0.0038 | 0.0031 | n.d. | 0.0079 |
| Myristic acid (C14:0) | 0.0115 | 0.0026 | 0.0049 | 0.0011 | 0.0349 | 0.0446 | 0.0059 | 0.0209 | n.d. | 0.0010 | 0.0087 | 0.0048 | n.d. | 0.0245 |
| Pentadecanoic acid (C15:0) | 0.0040 | 0.0021 | 0.0012 | 0.0003 | 0.0007 | 0.0012 | n.d. | n.d. | n.d. | n.d. | 0.0024 | n.d. | n.d. | n.d. |
| Palmitic acid (C16:0) | 0.3122 | 0.2478 | 0.0111 | 0.0216 | 0.3202 | 0.5740 | 0.0696 | 0.2865 | 0.0062 | 0.0243 | 0.0995 | 0.0866 | 0.0024 | 0.3393 |
| Palmitoleic acid (C16:1) | 0.0161 | 0.0097 | 0.0395 | 0.0129 | 0.0033 | 0.0067 | 0.0079 | 0.0276 | n.d. | 0.0023 | 0.0130 | 0.0077 | n.d. | 0.0325 |
| Margaric acid (C17:0) | 0.0045 | 0.0029 | 0.0002 | 0.0004 | 0.0002 | 0.0005 | n.d. | n.d. | n.d. | n.d. | 0.0049 | n.d. | n.d. | n.d. |
| Heptadecenoic acid (C17:1 ω-7) | 0.0014 | 0.0008 | 0.0012 | 0.0049 | 0.0004 | 0.0009 | n.d. | n.d. | n.d. | n.d. | 0.0035 | n.d. | n.d. | n.d. |
| Stearic acid (C18:0) | 0.0705 | 0.0601 | 0.0014 | 0.0026 | 0.0111 | 0.0247 | 0.0587 | 0.1878 | 0.0006 | 0.0110 | 0.0672 | 0.0575 | 0.0004 | 0.2280 |
| Oleic acid (C18:1ω-9) | 0.1314 | 0.1074 | 0.0782 | 0.0409 | 0.2137 | 0.4091 | 0.0725 | 0.2812 | n.d. | 0.0206 | 0.0955 | 0.1064 | n.d. | 0.2964 |
| Linoleic acid (C18:2) | 0.1499 | 0.1222 | n.d. | 0.0307 | 1.3673 | 1.5140 | 0.0306 | 0.1008 | 0.0077 | 0.0002 | 0.1271 | 0.0314 | n.d. | 0.1613 |
| α-linolenic acid (C18:3) | 0.0126 | 0.0086 | n.d. | 0.0151 | 0.0757 | 0.0795 | n.d. | n.d. | n.d. | n.d. | 0.0048 | n.d. | n.d. | n.d. |
| γ-Linolenic acid (C18:3) | n.d. | n.d. | n.d. | n.d. | n.d. | n.d. | n.d. | n.d. | n.d. | n.d. | n.d. | n.d. | n.d. | n.d. |
| Arachidic acid (C20:0) | 0.0007 | 0.0003 | n.d. | n.d. | n.d. | n.d. | n.d. | n.d. | n.d. | n.d. | 0.0002 | n.d. | n.d. | n.d. |
| Eicosadienoic acid (C20:2 ω-6) | 0.0018 | 0.0011 | n.d. | 0.0002 | 0.0002 | 0.0003 | 0.0005 | 0.0020 | n.d. | 0.0001 | 0.0007 | 0.0003 | n.d. | 0.0014 |

TABLE 8-continued

List of fatty acid compositions of all albumin used, n.d., not detected

| Fatty Acid (molar ratio) | pHSA | pHSA (de-fatted) | rHSA (S. cere-visiae) | rHSA (P. pastoris) | rHSA (O. sativa) Cella-stim | rHSA (O. sativa)* Cella-stim S | de-Albu-min-I | de-Albu-min-II | rHSA (Opti-bumin) | de-Albu-min-III | BSA | deBSA-I | BSA-Free | de-Albu-min-IV |
|---|---|---|---|---|---|---|---|---|---|---|---|---|---|---|
| Eicosatrienoic acid (C20:3 ω-3) | n.d. | n.d. | n.d. | n.d. | n.d. | n.d. | n.d. | n.d. | n.d. | n.d. | n.d. | n.d. | n.d. | n.d. |
| Bishomo-γ-linolenic acid (C20:3 ω-6) | 0.0025 | 0.0014 | n.d. | n.d. | n.d. | n.d. | 0.0006 | 0.0017 | n.d. | n.d. | 0.0020 | 0.0003 | n.d. | 0.0017 |
| Arachidonic acid (C20:4) | 0.0209 | 0.0094 | n.d. | 0.0011 | n.d. | n.d. | 0.0033 | 0.0088 | n.d. | n.d. | 0.0057 | 0.0012 | n.d. | 0.0090 |
| Eicosapentaenoic acid (C20:5 ω-3) | 0.0033 | 0.0010 | n.d. | n.d. | n.d. | n.d. | n.d. | n.d. | n.d. | n.d. | 0.0009 | n.d. | n.d. | n.d. |
| Behenic acid (C22:0) | 0.0005 | n.d. | n.d. | n.d. | n.d. | n.d. | n.d. | n.d. | n.d. | n.d. | 0.0003 | n.d. | n.d. | n.d. |
| Docosatetraenoic acid (C22:4 ω-6) | 0.0014 | 0.0008 | n.d. | n.d. | n.d. | n.d. | 0.0009 | 0.0024 | n.d. | n.d. | 0.0013 | n.d. | n.d. | 0.0021 |
| Docosapentaenoic acid (C22:5 ω-3) | 0.0015 | 0.0007 | n.d. | n.d. | n.d. | n.d. | n.d. | n.d. | n.d. | n.d. | 0.0010 | n.d. | n.d. | n.d. |
| Docosahexaenoic acid (C22:6 ω-3) | 0.0084 | 0.0031 | n.d. | n.d. | n.d. | n.d. | 0.0004 | 0.0011 | n.d. | n.d. | n.d. | n.d. | n.d. | 0.0010 |
| Lignoceric acid (C24:0) | n.d. | n.d. | n.d. | n.d. | n.d. | n.d. | n.d. | n.d. | n.d. | n.d. | n.d. | n.d. | n.d. | n.d. |
| Cerotic acid (C26:0) | n.d. | n.d. | n.d. | n.d. | n.d. | n.d. | n.d. | n.d. | n.d. | n.d. | n.d. | n.d. | n.d. | n.d. |
| Total (mol/mol HSA) | 0.7648 | 0.5821 | 0.1465 | 0.1462 | 2.0290 | 2.6596 | 0.2530 | 0.9284 | 0.0145 | 0.0606 | 0.4426 | 0.2993 | 0.0028 | 1.1051 |
| Total (mg/g HSA) | 3.09 | 2.36 | 0.58 | 0.58 | 8.35 | 10.90 | 1.03 | 3.77 | 0.06 | 0.24 | 1.81 | 1.22 | 0.01 | 4.49 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising:
a) an albumin polypeptide;
b) a fatty acid having less than 18 carbon atoms, which is present at a molar ratio to the albumin polypeptide ranging from about 0.02 to about 0.4; and
c) a fatty acid having 18 carbon atoms or more, which is present at a molar ratio to the albumin polypeptide ranging from about 0.03 to about 0.6, wherein the composition is substantially free of pentadecanoic acid (C15:0), margaric acid (C17:0), and heptadecenoic acid (C17:1 ω-7).

2. The composition of claim 1, wherein the fatty acid having less than 18 carbon atoms is selected from the group consisting of: lauric acid (C12:0), myristic acid (C14:0), palmitic acid (C16:0), and palmitoleic acid (C16:1).

3. The composition of claim 1, wherein the composition comprises lauric acid (C12:0), myristic acid (C14:0), palmitic acid (C16:0), and palmitoleic acid (C16:1).

4. The composition of claim 1, wherein the fatty acid having 18 carbon atoms or more is selected from the group consisting of: stearic acid (C18:0), oleic acid (C18:1ω-9), linoleic acid (C18:2), and eicosadienoic acid (C20:2 ω-6).

5. The composition of claim 1, wherein the composition comprises stearic acid (C18:0), oleic acid (C18:1ω-9), linoleic acid (C18:2), and eicosadienoic acid (C20:2 ω-6).

6. The composition of claim 1, wherein the composition comprises one or more fatty acids selected from the group consisting of: bishomo-γ-linolenic acid (C20:3 ω-6), arachidonic acid (C20:4), docosatetraenoic acid (C22:4 ω-6), and docosahexaenoic acid (C22:6 ω-3).

7. The composition of claim 1, wherein the composition comprises lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 ω-6), arachidonic acid (C20:4), docosatetraenoic acid (C22:4 ω-6), and docosahexaenoic acid (C22:6 ω-3).

8. The composition of claim 1, wherein the composition comprises lauric acid (C12:0), myristic acid (C14:0), palmitic acid (C16:0), palmitoleic acid (C16:1), stearic acid (C18:0), oleic acid (C18:1ω-9), linoleic acid (C18:2), and eicosadienoic acid (C20:2 ω-6).

9. The composition of claim 1, wherein the composition comprises lauric acid (C12:0), myristic acid (C14:0), palmitic acid (C16:0), palmitoleic acid (C16:1), stearic acid (C18:0), oleic acid (C18:1ω-9), linoleic acid (C18:2), eicosadienoic acid (C20:2 ω-6), bishomo-γ-linolenic acid (C20:3 ω-6), and arachidonic acid (C20:4).

10. The composition of claim 1, wherein a total molar ratio of fatty acid to the albumin polypeptide is less than 1.

11. The composition of claim 1, wherein the composition is substantially free of α-linolenic acid (C18:3), γ-linolenic acid (C18:3), arachidic acid (C20:0), eicosatrienoic acid (C20:3 ω-3), eicosapentaenoic acid (C20:5 ω-3), behenic acid (C22:0), docosapentaenoic acid (C22:5 ω-3), lignoceric acid (C24:0), and/or cerotic acid (C26:0).

12. A composition comprising:
a) an albumin polypeptide; and
b) one or more fatty acids,
wherein the composition is substantially free of pentadecanoic acid (C15:0), margaric acid (C17:0), heptadecenoic acid (C17:1 ω-7), α-linolenic acid (C18:3), γ-linolenic acid (C18:3), arachidic acid (C20:0), eicosatrienoic acid (C20:3 ω-3), eicosapentaenoic acid (C20:5 ω-3), behenic acid (C22:0), docosapentaenoic acid (C22:5 ω-3), lignoceric acid (C24:0), and cerotic acid (C26:0), and
wherein a total molar ratio of the one or more fatty acids to the albumin polypeptide is from about 0.05 to about 1.

13. The composition of claim 1, wherein the albumin polypeptide is derived from human or bovine.

14. The composition of claim 1, wherein the albumin polypeptide is a recombinant albumin polypeptide.

15. The composition of claim 1, wherein the albumin polypeptide is derived from plasma or serum.

16. The composition of claim 1, wherein the albumin polypeptide is a defatted albumin polypeptide.

17. A method comprising: incubating biological cells in a cell culture medium comprising the composition of claim 1 and a basal medium.

18. The method of claim 17, wherein the biological cells are eukaryotic cells.

19. The method of claim 18, wherein the eukaryotic cells are selected from the group consisting of: stem cells, T-cells, and neuronal cells.

20. The method of claim 19, wherein the stem cells are induced pluripotent stem (iPS) cells, embryonic stem (ES) cells, or mesenchymal stem cells (MSCs).

21. The method of claim 17, wherein the method results in an increase in viable cell density of the biological cells as compared to biological cells cultured in an absence of albumin polypeptide.

22. The method of claim 17, wherein the method results in an increase in viable cell density by at least 35% of induced pluripotent stem (iPS) cells upon culturing the iPS cells in the composition for a duration of 4 days, as compared to a composition lacking the recombinant albumin polypeptide.

23. The method of claim 17, wherein the method results in an increase in viable cell density by at least 35% of mesenchymal stem cells (MSCs) upon culturing the MSCs in the composition for a duration of 5 days, as compared to a composition lacking the recombinant albumin polypeptide.

24. The method of claim 17, wherein the method results in an increase in viable cell density by at least 80% of T-cells upon culturing the T-cells are cultured in the composition for a duration of 6 days, as compared to a composition lacking the recombinant albumin polypeptide.

* * * * *

SEQUENCE LISTING

```
<160> NUMBER OF SEQ ID NOS: 2

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60
```

-continued

```
Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
```

```
                     485                 490                 495
Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 2
<211> LENGTH: 607
<212> TYPE: PRT
<213> ORGANISM: Bos taurus

<400> SEQUENCE: 2

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
```

-continued

```
                    245                 250                 255
Leu Val Thr Asp Leu Thr Lys Val His Lys Glu Cys Cys His Gly Asp
                260                 265                 270
Leu Leu Glu Cys Ala Asp Asp Arg Ala Asp Leu Ala Lys Tyr Ile Cys
            275                 280                 285
Asp Asn Gln Asp Thr Ile Ser Ser Lys Leu Lys Glu Cys Cys Asp Lys
        290                 295                 300
Pro Leu Leu Glu Lys Ser His Cys Ile Ala Glu Val Glu Lys Asp Ala
305                 310                 315                 320
Ile Pro Glu Asn Leu Pro Pro Leu Thr Ala Asp Phe Ala Glu Asp Lys
                325                 330                 335
Asp Val Cys Lys Asn Tyr Gln Glu Ala Lys Asp Ala Phe Leu Gly Ser
            340                 345                 350
Phe Leu Tyr Glu Tyr Ser Arg Arg His Pro Glu Tyr Ala Val Ser Val
        355                 360                 365
Leu Leu Arg Leu Ala Lys Glu Tyr Glu Ala Thr Leu Glu Glu Cys Cys
    370                 375                 380
Ala Lys Asp Asp Pro His Ala Cys Tyr Ser Thr Val Phe Asp Lys Leu
385                 390                 395                 400
Lys His Leu Val Asp Glu Pro Gln Asn Leu Ile Lys Gln Asn Cys Asp
                405                 410                 415
Gln Phe Glu Lys Leu Gly Glu Tyr Gly Phe Gln Asn Ala Leu Ile Val
            420                 425                 430
Arg Tyr Thr Arg Lys Val Pro Gln Val Ser Thr Pro Thr Leu Val Glu
        435                 440                 445
Val Ser Arg Ser Leu Gly Lys Val Gly Thr Arg Cys Cys Thr Lys Pro
    450                 455                 460
Glu Ser Glu Arg Met Pro Cys Thr Glu Asp Tyr Leu Ser Leu Ile Leu
465                 470                 475                 480
Asn Arg Leu Cys Val Leu His Glu Lys Thr Pro Val Ser Glu Lys Val
                485                 490                 495
Thr Lys Cys Cys Thr Glu Ser Leu Val Asn Arg Arg Pro Cys Phe Ser
            500                 505                 510
Ala Leu Thr Pro Asp Glu Thr Tyr Val Pro Lys Ala Phe Asp Glu Lys
        515                 520                 525
Leu Phe Thr Phe His Ala Asp Ile Cys Thr Leu Pro Asp Thr Glu Lys
    530                 535                 540
Gln Ile Lys Lys Gln Thr Ala Leu Val Glu Leu Leu Lys His Lys Pro
545                 550                 555                 560
Lys Ala Thr Glu Glu Gln Leu Lys Thr Val Met Glu Asn Phe Val Ala
                565                 570                 575
Phe Val Asp Lys Cys Cys Ala Ala Asp Asp Lys Glu Ala Cys Phe Ala
            580                 585                 590
Val Glu Gly Pro Lys Leu Val Val Ser Thr Gln Thr Ala Leu Ala
        595                 600                 605
```